United States Patent
Tass

(10) Patent No.: US 9,486,389 B2
(45) Date of Patent: Nov. 8, 2016

(54) APPARATUS AND METHOD FOR CALIBRATING NON-INVASIVE DESYNCHRONIZING NEUROSTIMULATION

(71) Applicant: Forschungszentrum Juelich GmbH, Juelich (DE)

(72) Inventor: Peter Alexander Tass, Juelich (DE)

(73) Assignee: Forschungszentrum Juelich GmbH, Juelich (DE)

(*) Notice: Subject to any disclaimer, the term of this patent is extended or adjusted under 35 U.S.C. 154(b) by 27 days.

(21) Appl. No.: 14/376,960

(22) PCT Filed: Feb. 7, 2013

(86) PCT No.: PCT/EP2013/052450
§ 371 (c)(1),
(2) Date: Aug. 6, 2014

(87) PCT Pub. No.: WO2013/117655
PCT Pub. Date: Aug. 15, 2013

(65) Prior Publication Data
US 2015/0297444 A1 Oct. 22, 2015

(30) Foreign Application Priority Data
Feb. 8, 2012 (DE) .................. 10 2012 002 436

(51) Int. Cl.
*A61N 1/36* (2006.01)
*A61H 23/00* (2006.01)
(Continued)

(52) U.S. Cl.
CPC .......... *A61H 23/00* (2013.01); *A61B 5/04008* (2013.01); *A61B 5/0476* (2013.01);
(Continued)

(58) Field of Classification Search
CPC .. A61N 1/361; A61B 5/128; A61B 5/04845; A61B 5/4064; A61B 5/40; A61B 5/4076; A61B 5/4082; A61B 5/4088; A61M 2021/0027; H04R 25/75; A61F 11/04
See application file for complete search history.

(56) References Cited

U.S. PATENT DOCUMENTS 8,423,144 B2 4/2013 Tass et al.
8,543,219 B2 9/2013 Tass
(Continued)

FOREIGN PATENT DOCUMENTS

DE 102 33 960 A1 2/2004
DE 102008012669 A1 9/2009
(Continued)

OTHER PUBLICATIONS

Tass, PA. "Stochastic phase resetting of two coupled phase oscillators stimulated at different times." Phys Rev E Stat Nonlin Soft Matter Phys. May 2003;67(5 Pt 1):051902. Epub May 6, 2003.*
(Continued)

*Primary Examiner* — Eugene Wu
(74) *Attorney, Agent, or Firm* — Arent Fox LLP

(57) ABSTRACT

The invention relates to an apparatus (1) for stimulating neurons having a pathological synchronous and oscillatory neural activity, said apparatus comprising a non-invasive stimulation unit (11) for applying stimuli (22) that stimulate a patient's neurons, a measurement unit (12) for recording test signals (23) that represent a neural activity of the stimulated neurons, and a control and analysis unit (10) for controlling the stimulation unit (11) and analyzing the test signals (23). The stimulation unit (11) applies first stimuli (34), and based on the test signals (23) recorded in reaction to the application of the first stimuli (34), the first stimuli (34) causing the phase of the pathological synchronous and oscillatory neural activity of the stimulated neurons to be reset are selected, whereupon the stimulation unit (11) applies the selected first stimuli (34) with a time delay, and the test signals (23) recorded in reaction to the stimuli (34, 38) applied with the time delay are used to verify whether said stimuli (34, 38) applied with the time delay suppress the pathological synchronous and oscillatory neural activity of the stimulated neurons.

9 Claims, 13 Drawing Sheets

(51) Int. Cl.
  *A61B 5/04* (2006.01)
  *A61B 5/0476* (2006.01)
  *A61F 7/00* (2006.01)
  *A61N 5/06* (2006.01)
  *A61B 5/00* (2006.01)

(52) U.S. Cl.
  CPC ............ *A61F 7/00* (2013.01); *A61N 1/36014* (2013.01); *A61N 1/36025* (2013.01); *A61N 5/0622* (2013.01); *A61B 5/742* (2013.01); *A61B 5/7405* (2013.01); *A61B 5/7455* (2013.01); *A61N 2005/0626* (2013.01); *A61N 2005/0648* (2013.01)

(56) References Cited

U.S. PATENT DOCUMENTS

| | | | |
|---|---|---|---|
| 2006/0047324 A1* | 3/2006 | Tass | A61B 5/0482 607/45 |
| 2006/0212089 A1* | 9/2006 | Tass | A61N 1/36017 607/45 |
| 2010/0331912 A1 | 12/2010 | Tass et al. | |
| 2011/0009921 A1* | 1/2011 | Tass | A61B 5/486 607/45 |
| 2011/0201977 A1* | 8/2011 | Tass | A61H 7/004 601/15 |
| 2013/0041296 A1 | 2/2013 | Tass et al. | |
| 2015/0018898 A1* | 1/2015 | Tass | A61N 1/36064 607/62 |

FOREIGN PATENT DOCUMENTS

| | | |
|---|---|---|
| DE | 102008015259 A1 | 9/2009 |
| DE | 102010000390 A1 | 8/2011 |
| DE | 10 2010 016 461 A1 | 10/2011 |
| WO | WO-2004/093981 A1 | 11/2004 |
| WO | WO-2011/127917 A2 | 10/2011 |

OTHER PUBLICATIONS

Bilecen et al. "Tonotopic organization of the human auditory cortex as detected by BOLD-FMRI". Hearing Research vol. 126, Issues 1-2, Dec. 1998, pp. 19-27.*

International Search Report for PCT/EP2013/052450, dated Jul. 31, 2013.

B. Lysyansky et al.; "Desynchronizing anti-resonance effect of m: n ON-OFF corrdinated reset stimulation"; Journal of Neural Engineering 8, 2011, pp. 1-13.

P.A. Tass; "Desynchronizing double-pulse phase resetting and application to depp brain stimulation"; Biological Cybernetics, Springer-Verlag, Heidelberg, Germany, vol. 85, No. 5, Nov. 1, 2001, pp. 343-354.

P.A. Tass; "A model of desynchronizing deep brain stimulation with a demand-controlled coordinated reset of neural subpopulations"; Biological Cybernetics 89, 2003, pp. 81-88.

P. A. Tass; "Stochastic phase of two coupled phase oscillators stimulated at different times"; Physical Review E 67, 2003, pp. 051902-1-051902-15.

N.E. Huang et al.; "The empirical mode decomposition and the Hilbert spectrum for nonlinear and non-stationary time series analysis"; Proceedings of Royal Society of London Series A, 1998, vol. 454, pp. 903-995.

N.E. Huang et al.; "A confidence limit for the empirical mode decomposition and Hilbert spectral analysis"; Proceedings of the Royal Society of London Series A, 2003, vol. 459, pp. 2317-2345.

P.A. Tass; "Desynchronization of brain rhythms with soft phase-resetting techniques"; Biological Cybernetics 87, 2002, pp. 102-115.

P.A. Tass et al.; "Detection of n:m Phase Locking from Noisy Data: Application to Magnetoencephalography"; Physical Review Letters, vol. 81, No. 15, 1998, pp. 3291-3294.

D. Bilecen et al.; "Tonotopic organization of the human auditory cortex as detected by BOLD-FMRI"; Hearing Research 126, 1998, pp. 19-27.

Dave R. M. Langers et al.; "Representation of lateralization nad tonotopy in primary versus secondary human auditory cortex"; NeuroImage 34, 2007, pp. 264-273.

W. Mühlnickel et al.; "Reorganization of auditory cortex in tinnitus"; Proc. Natl. Acad. Sci. USA, vol. 95, Aug. 1998, pp. 10340-10343.

B.A. Wandell et al.; "Visual Field Maps in Human Cortex"; Neuron 56, Oct. 2007, pp. 366-383.

A. Benninghoff et al.; "Lehrbuch der Anatomie des Menschen. Dargestellt unter Bevorzugung funktioneller Zusammenhänge. 3. Bd. Nervensystem, Haut und Sinnesorgane", [Textbook of Human Anatomy. Presented With Emphasis on Functional Relatonships. 3rd vol., Nervous System, Skin and Sensory Organs ], Urban und Schwarzenberg, Munich 1964, pp. 126-137 (Described in specification, p. 53, lines 15-26).

* cited by examiner

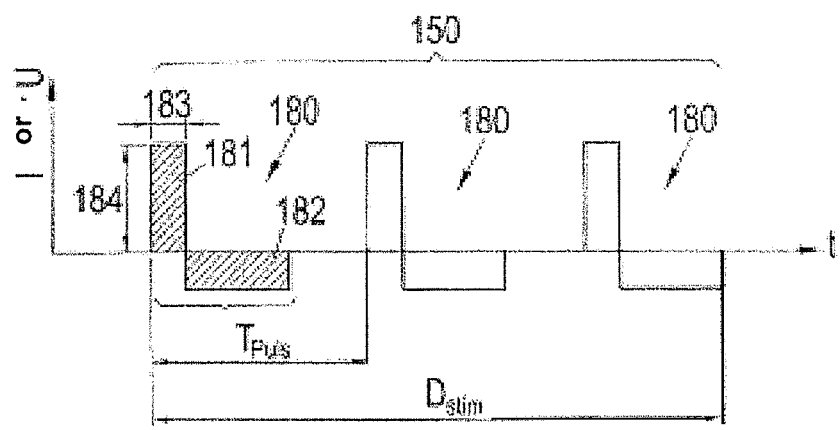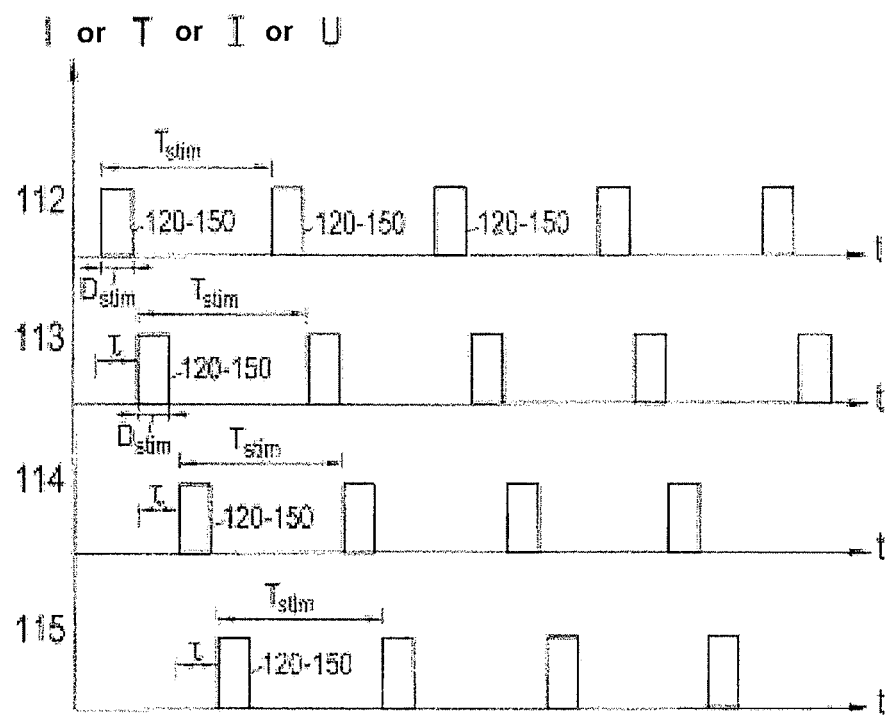

APPARATUS AND METHOD FOR CALIBRATING NON-INVASIVE DESYNCHRONIZING NEUROSTIMULATION

FIELD OF TECHNOLOGY

The relates to an apparatus and to a method for calibrating non-invasive desynchronizing neurostimulation.

BACKGROUND OF THE INVENTION

Nerve cell structures in circumscribed regions of the brain are pathologically, e.g. excessively synchronously, active in patients with neurological or psychiatric diseases such as Parkinson's disease, essential tremor, tinnitus, dystonia or obsessive compulsive disorders. In this case, a large number of neurons synchronously form action potentials, i.e. the participating neurons fire excessively synchronously. In a healthy person, in contrast, the neurons fire with a different quality, i.e. in an uncorrelated manner, in these brain sectors.

Stimulation techniques have been developed for treating such diseases which directly counteract pathologically synchronous neural activity. In particular the coordinated reset (CR) stimulation is in this respect characterized by great therapeutic effectiveness and reliability (cf. e.g. "A model of desynchronizing deep brain stimulation with a demand-controlled coordinated reset of neural subpopulations" by P. A. Tass, published in Biol. Cybern. 89, 2003, pages 81 to 88). The CR stimulation can be realized with different stimulus modalities, e.g. by means of electrical stimulation or sensory, e.g. acoustic, stimulation. The non-invasive stimulation processes and apparatus are particularly promising since they are much lower in side effects and are less expensive (and are thus accessible for a larger number of patients).

It is important for the effectiveness of the CR stimulation that the different sites in the brain or spinal cord which are stimulated by the stimulation lie in the neural population to be stimulated (or, in invasive CR stimulation, in the fiber bundle to be stimulated). In invasive CR stimulation, the ideal localization of the implanted electrode is ensured within the framework of the surgical planning, inter alia via detailed anatomical information, e.g. from magnetic resonance imaging examinations.

In the non-invasive stimulation processes, in contrast, the selection of the ideal stimulation sites in the brain or spinal cord which corresponds to a calibration of stimulation parameters, e.g. the pitches of the therapeutic tones in acoustic CR stimulation, or to a calibration of the localization of the different non-invasive actuators (e.g. the placement of the vibro-tactile stimulators on the skin in relation to the affected body part), is a problem yet to be solved. Time-consuming trial and error does not guarantee the ideal effectiveness of the non-invasive CR therapy since, on the one hand, not all possible stimulation sites in the brain are systematically developed and tested and, on the other hand, the patients are stressed by long examinations so that the cooperation of the patients naturally suffers and the results of the test become worse.

SUMMARY OF THE INVENTION

It is the underlying object of the invention to provide an apparatus and a method which allow a calibration of the stimulation parameters independent of the examiner, carried out automatically and on an electrophysiological basis. This calibration should in particular make it possible (i) to carry out the therapy effectively; (ii) to avoid side effects; and (iii) to make the examination to be carried out for the parameter setting as short, practical and tolerable as possible for the patient.

The object underlying the invention is satisfied by the features of the independent claims. Advantageous further developments and aspects of the invention are set forth in the dependent claims.

BRIEF DESCRIPTION OF THE DRAWINGS

The invention will be described in more detail in the following in an exemplary manner with reference to the drawings. There are shown in these:

FIG. 20 a schematic representation of an electrical transcutaneous stimulus;

FIG. 21 a schematic representation of tactile, vibratory, thermal and/or electrical transcutaneous CR neurostimulation.

DETAILED DESCRIPTION OF THE EMBODIMENTS

Figure 1:
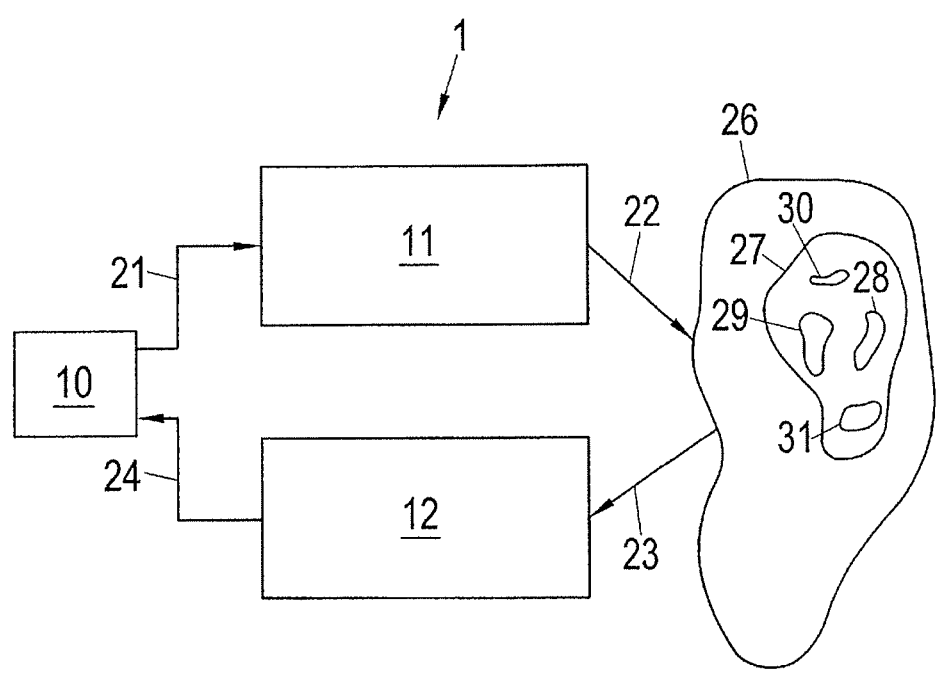
FIG. 1 a schematic representation of an apparatus for non-invasive desynchronizing neurostimulation during operation.

An apparatus 1 for calibrating the stimulation parameters of a non-invasive desynchronizing neurostimulation is shown schematically in FIG. 1. The apparatus 1 comprises a control and analysis unit 10, a stimulation unit 11 and a measuring unit 12. During the operation of the apparatus 1, the control and analysis unit 10 inter alia carries out a control of the stimulation unit 11. For this purpose, the control and analysis unit 10 generates control signals 21 which are received by the stimulation unit 11. The stimulation unit 11 generates stimuli 22 using the control signals 21 and administers them to a patient. The stimuli 22 can be stimuli from the group of acoustic, optical, tactile, vibratory, thermal and electrical transcutaneous stimuli. The stimuli 22 can in particular be consciously perceivable by the patient. The stimulation unit 11 and in particular also the control and analysis unit 10 are non-invasive units, i.e. they are located outside the body of the patient during the operation of the apparatus 1 and are not surgically implanted in the body of the patient.

The stimulation effect achieved by the stimuli 22 is monitored with the aid of the measuring unit 12. The measuring unit 12 records one or more measured signals 23 measured at the patient, converts them as required into electrical signals 24 and supplies them to the control and analysis unit 10. The neural activity in the stimulated target zone or in a zone associated with the target zone can in particular be measured by means of the measuring unit 12, with the neural activity of this zone correlating sufficiently closely with the neural activity of the target zone (e.g. muscle activity). The control and analysis unit 10 processes the signals 24, e.g. the signals 24 can be amplified and filtered, and analyzes the processed signals 24. The control and analysis unit 10 in particular controls the stimulation unit 11 with reference to the results of this analysis. The control and analysis unit 10 can include e.g. a processor (e.g. a microcontroller) for carrying out its work.

The measuring unit 12 includes one or more sensors which in particular make possible (i) a stimulus-induced reset of the phase of the pathological oscillatory activity and (ii) a detection of a decrease or increase in the amplitude of the pathological oscillatory activity.

Non-invasive sensors can be used as the sensors, e.g. electroencephalograph (EEG) electrodes, magnetic encephalograph (MEG) sensors and sensors for measuring local field potentials (LFPs). The neural activity can also be determined indirectly by measurement of the accompanying muscle activity by means of electromyography (EMG).

Alternatively, the sensors can be implanted in the body of the patient. Epicortical electrodes, deep-brain electrodes, subdural or epidural brain electrodes, subcutaneous EEG electrodes and subdural or epidural spinal cord electrodes can serve as invasive sensors, for example. Furthermore, electrodes to be fastened to peripheral nerves can be used as sensors.

Provision can by all means be made that the individual components of the apparatus 1, in particular the control and analysis unit 10, the stimulation unit 11 and/or the measuring unit 12, are separate from one another construction-wise. The apparatus 1 can therefore also be understood as a system.

The apparatus 1 can in particular be used for treating neurological or psychiatric diseases, e.g. Parkinson's disease, essential tremor, tremor resulting from multiple sclerosis as well as other pathological tremors, dystonia, epilepsy, depression, locomotor disorders, cerebellar diseases, obsessive compulsive disorders, Tourette's syndrome, autism, functional disorders after stroke, spasticity, tinnitus, sleep disorders, schizophrenia, irritable bowel syndrome, addiction diseases, borderline personality disorder, attention deficit syndrome, attention deficit hyperactivity syndrome, pathological gambling, neuroses, bulimia, anorexia, eating disorders, burnout syndrome, fibromyalgia, migraine, cluster headache, general headache, neuralgia, ataxia, tic disorder or hypertension as well as further diseases which are characterized by pathologically increased neural synchronization.

The aforesaid diseases can be caused by a disorder of the bioelectric communication of neural assemblies which are connected in specific circuits. In this respect, a neural population continuously generates pathological neural activity and possibly a pathological connectivity associated therewith (network structure). In this respect, a large number of neurons synchronously form action potentials, i.e. the participating neurons fire excessively synchronously. In addition, there is the fact that the pathological neural population has an oscillatory neural activity, i.e. the neurons fire rhythmically. In the case of neurological or psychiatric diseases, the mean frequency of the pathological rhythmic activity of the affected neural assemblies lies approximately in the range from 1 to 30 Hz, but can also be outside this range. In healthy people, the neurons fire qualitatively differently, in contrast, e.g. in an uncorrelated manner.

The apparatus 1 is shown during a CR stimulation in FIG. 1. At least one neural population 27 in the brain 26 or in the spinal cord 26 of the patient has a pathologically synchronous and oscillatory neural activity as described above. The stimulation unit 11 administers the stimuli 22 to the patient such that the stimuli 22 are received via the patient's eyes, ears or skin depending on the modality and are forwarded from there via the nervous system to the pathologically active neural population 27 in the brain 26 and/or spinal cord 26. The stimuli 22 are designed such that the pathologically synchronous activity of the neural population 27 is desynchronized. A lowering of the coincidence rate of the neurons effected by the stimulation can result in a lowering of the synaptic weights and thus in an unlearning of the tendency to produce pathologically synchronous activity.

On the application of acoustic (or auditory) or optical (or visual) stimuli 22, they are received via at least one ear or at least one eye of the patient. The tactile, vibratory, thermal and electrical transcutaneous stimuli 22 are received by receptors disposed in or beneath the skin and are forwarded to the nervous system. These receptors include, for example, Merkel cells, Ruffini corpuscles, Meissner corpuscles and hair follicle receptors which in particular act as receptors for the tactile stimuli 22. The vibratory stimuli 22 are predominantly directed to proprioception. The vibratory stimuli 22 can be received by receptors disposed in the skin, in the muscles, in the subcutaneous tissue and/or in the sinews of the patient. Vater-Pacini corpuscles can be named by way of example as receptors for the vibratory stimuli 22 which communicate vibration perceptions and accelerations. The thermal stimuli 22 are received by the thermoreceptors of the skin. They are warm receptors (also called heat receptors, warm sensors or heat sensors) and cold sensors (also called cold receptors). The cold sensors are more superficial in the skin of people; the heat receptors somewhat lower. The electrical transcutaneous stimuli 22 do not act specifically on only one group of receptors disposed in or beneath the skin. The target zone can therefore be stimulated via different channels using the electrical transcutaneous stimuli 22.

The directed stimulation of specific regions of the brain or spinal cord is made possible by the tonotopic or somatotopic association of body regions with these regions. For example, acoustic stimuli are converted into nerve impulses in the inner ear and are forwarded via the acoustic nerve to the auditory cortex. A specific portion of the auditory cortex is activated on the acoustic stimulation of the inner ear at a specific frequency due to the tonotopic arrangement of the auditory cortex.

On the visual stimulation, different points in the visual field are imaged on different points of the retina via the crystalline lens of the eye. The different points of the retina are in turn connected via the optic nerve to different neurons in the brain. Consequently, respective different neurons can be stimulated using the stimuli applied at different spatial sites.

Due to the somatotopic structuring of the neural pathways and of the associated zones of the brain, different neurons are furthermore stimulated by tactile, vibratory, thermal and electrical transcutaneous stimuli which are applied at different sites on the skin. With these types of stimulation, the stimulation elements can be attached, for example, to the foot, lower leg and thigh or to the hand, the lower arm and upper arm of the patient in order thereby to be able to stimulate specific neurons.

The stimulation unit 11 can accordingly separately stimulate different regions of the brain 26 or spinal cord 26 in that the applied stimuli 22 are forwarded via neural conductors to different target zones which lie in the brain 26 and/or spinal cord 26. The target zones can be stimulated with possibly different and/or time-offset stimuli 22 during the CR stimulation.

In the CR stimulation, stimuli 22 which effect a reset of the phase of neural activity of the stimulated neurons in the neural population 27 are administered to the neural population 27 which has a pathologically synchronous and oscillatory activity. The phase of the stimulated neurons is set to or close to a specific phase value, e.g. 0° (it is not possible in practice to set a specific phase value exactly; however, this is also not required for a successful CR stimulation) by the reset, independently of the current phase value. The phase of the neural activity of the pathological neural population 27 is thus controlled by means of a direct stimulation. Since it is furthermore possible to stimulate the pathological neural population 27 at different sites, the phase of neural activity of the pathological neural population 27 can be reset at the different stimulation sites at different points in time. As a result, the pathological neural population 27 whose neurons were previously synchronous and active at the same frequency and phase is split into a plurality of subpopulations which are shown schematically in FIG. 1 and are marked by the reference numerals 28, 29, 30 and 31 (four subpopulations are shown by way of example here). Within one of the subpopulations 28 to 31, the neurons are still synchronous after the resetting of the phase and also still fire at the same pathological frequency, but each of the subpopulations 28 to 31 has the phase with respect to their neural activity which was enforced by the stimulation stimulus. This means that the neural activities of the individual subpopulations 28 to 31 still have the same approximately sinusoidal curve at the same pathological frequency, but different phases, after the resetting of their phases.

Due to the pathological interaction between the neurons, the state with at least two subpopulations generated by the stimulation is unstable and the total neural population 27 fast approaches a state of complete desynchrononization in which the neurons fire without correlation. The desired state i.e. the complete dresynchronization is thus not immediately present after the time-offset (or phase-shifted) application of the phase-resetting stimuli 22, but is usually adopted within a few periods or even in less than one period of the pathological frequency.

One theory for explaining the stimulation success is based on the fact that the ultimately desired desynchronization is only made possible by the pathologically increased interaction between the neurons. In this respect, a self-organization process is made use of which is responsible for the pathological synchronization. It also has the effect that a division of an overall population 27 into subpopulations 28 to 31 with different phases is followed by a desynchronization. In contrast to this, no desynchronization would take place without a pathologically increased interaction of the neurons.

Furthermore, a reorganization of the connectivity of the disturbed neural networks can be achieved by the CR stimulation so that long-lasting therapeutic effects can be brought about. The obtained synaptic conversion is of great importance for the effective treatment of neurological or psychiatric diseases.

Figure 2:
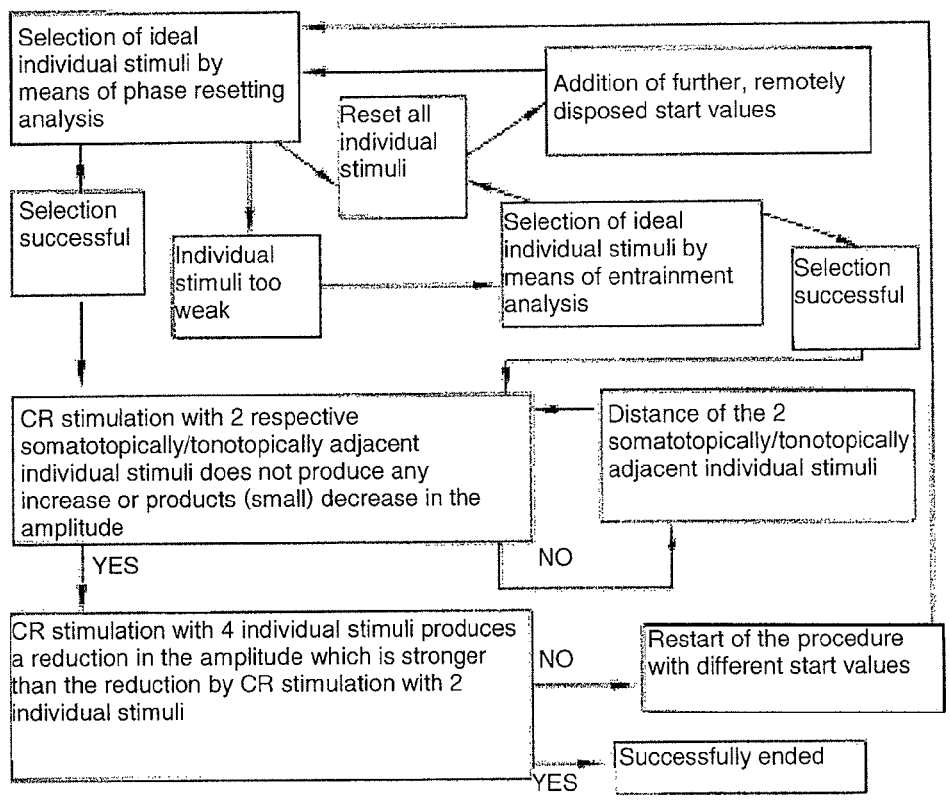
FIG. 2 a flowchart for illustrating the calibration of the apparatus shown in FIG. 1.

In the following, the calibration is described which is carried out using the apparatus 1 in order thus to determine the ideal stimulus parameters for the non-invasive CR stimulation. The steps carried out within the framework of this calibration are combined in the flowchart of FIG. 2.

In a first step, the stimulation unit 11 generates first stimuli 34 and administers them to the patient. It is the aim of this step to localize the synchronous focus in the brain or spinal cord. The first stimuli 34 can be predefined and in particular represent a preselection of possible individual stimuli whose efficacy is medically plausible in the CR stimulation. For example, such stimuli can be selected as first stimuli 34 with which a successful CR stimulation had been able to be carried out with another patient with the same or similar symptoms. The first stimuli 34 of the start selection each have a stimulus parameter which lies within a first stimulus parameter range.

In the case of acoustic stimulation, for example, therapeutic tones can be selected as first stimuli 34 in an interval about the dominant tinnitus frequency of the patient (with tonal tinnitus). In this case, the stimulus parameter consequently corresponds to a frequency and the first stimulus parameter range corresponds to a frequency interval. The interval of therapeutic tones can also be adapted to the extension of the high-frequency dip or hearing impairment (i.e. to include them). With patients with non-tonal tinnitus (hissing or noises), a starting value of the interval of CR therapeutic tones can originate from an audiometric comparison measurement (of the frequency interval of the tinnitus). However, standard intervals of CR therapeutic tones can also be selected for the kinds of ear noises typical in practice.

In the case of optical stimulation, a specific region of the visual field is selected as the first stimulus parameter range. Specific regions of the brain 26 are stimulated by the application of optical first stimuli 34 in this visual field region.

In the case of vibro-tactile or thermal or transcutaneous electrical stimulation, a skin area is selected as the first stimulus parameter range which includes the diseased body part (that is, is a little larger so that the actually required extent can be determined by the selection of the ideal individual stimuli) or includes representations (e.g. Head's zones) of the diseased body part or organ. The first stimuli 34 are applied within the selected skin area.

The one-dimensional start interval of tones or the two-dimensional visual field region or the two-dimensional start area of the skin can subsequently be covered by the first stimuli 34 in accordance with the physiological mapping characteristics familiar to the skilled person (e.g. in a first approximation logarithmic tonotopic map in the primary auditory cortex and along conditions, e.g. on the tactile skin stimulation) such that they cover the respective cortical representation equidistantly in a first approximation, i.e. the associated target sites in the brain or spinal cord which are stimulated by the first stimuli 34 should have the same spatial distances from one another, that is be equidistant, in a first approximation.

The first stimuli 34 are subsequently tested by the control and analysis unit 10 as to whether they can reset the phase of the pathological, synchronized and oscillatory brain activity. In this respect, those first stimuli 34 are selected from the preselection of first stimuli 34 which are able to reset the phase of the pathological, synchronized and oscillatory brain activity (or muscle activity). Methods for examining such a phase reset are familiar to the skilled person.

Figure 3:
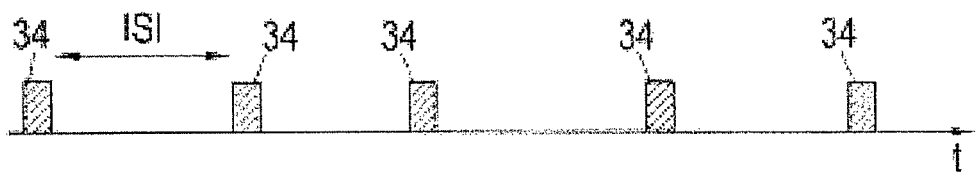
FIG. 3 a schematic representation of a stimulus sequence for analyzing the phase resetting effected by the stimuli.

The analysis of the phase reset of the synchronous neural activity typically takes place by means of an ensemble of identical first stimuli 34 (i.e. individual stimuli). Such an ensemble of first stimuli 24 is applied against the time t by way of example in FIG. 3. To avoid entrainment phenomena, an interstimulus interval ISI between the individual stimuli 34 of sufficiently large and randomized length should be observed. The mean interstimulus interval should be long enough in comparison with the actual stimulus response so that the stimulus responses do not overlap and have completely decayed on administration of the subsequent stimulus.

Figure 4:
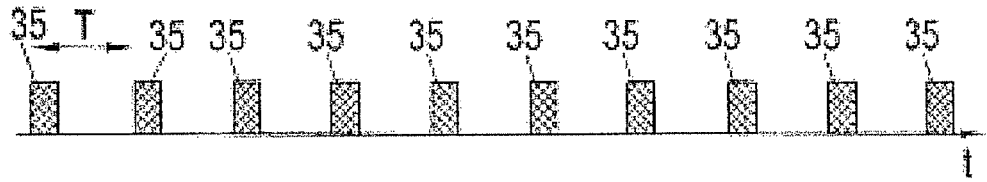
FIG. 4 a schematic representation of an entrainment stimulus sequence.

One possibility which is familiar to the skilled person for the analysis of the phase reset is described, for example, in the article "Stochastic phase resetting of two coupled phase oscillators stimulated at different times" by P. A. Tass (published in Physical Review E 67, 2003, pages 051902-1 to 051902-15). The phase resetting index is determined for this purpose (cf. equation 8, stimulus locking index for v=1). The phase used in this respect for calculating the phase resetting is e.g. determined using the Hilbert transformation from the signal which is determined using bandpass filtering or empirical mode decomposition and which represents the pathological oscillatory activity (the latter allows a parameter-independent determination of physiologically relevant modes in different frequency ranges in comparison with bandpass filtering, cf. "The empirical mode decomposition and the Hilbert spectrum for nonlinear and non-stationary time series analysis" by N. E. Huang et al. (published in Proceedings of the Royal Society of London Series A, 1998, Volume 454, pages 903 to 995); the combination of empirical mode decomposition with subsequent Hilbert transformation is called a Hilbert-Huang transformation, cf. "A confidence limit for the empirical mode decomposition and Hilbert spectral analysis" by N. E. Huang et al. (published in Proceedings of the Royal Society of London Series A, 2003, Volume 459, pages 2317 to 2345). A phase reset is achieved when the phase resetting index exceeds the 99th percentile of the prestimulus distribution of the phase resetting index (cf. FIG. 4 in "Stochastic phase resetting of two coupled phase oscillators stimulated at different times" by P. A. Tass). If a stronger phase resetting effect is medically desirable, higher thresholds can also be selected, e.g. twice to three times the 99th percentile of the prestimulus distribution of the phase resetting index.

Alternatively to this data analysis, simpler data analysis processes can also be used which are able to approximate the detection of phase resetting with a precision sufficient in practice. E.g. averaging can take place simply via the ensemble of stimulus responses. A phase resetting is then approximately to be assumed when the maximum amount of the stimulus response exceeds the 99th percentile of the prestimulus distribution of the averaged response (or double or three times it) (cf. FIG. 6 in "Stochastic phase resetting of two coupled phase oscillators stimulated at different times" by P. A. Tass).

If the first stimuli 34 are too low, i.e. if a phase reset can also not be achieved with a medium intensity (in accordance with physiological criteria) of the individual stimuli, a soft phase reset can be carried out which is, for example, known to the skilled person from the article "Desynchronization of brain rhythms with soft phase-resetting techniques" by P. A. Tass (published in Biol. Cybern. 87, 2002, pages 102 to 115) In this respect, the simulation unit 11 applies a periodic sequence of individual stimuli 35, which is shown schematically in FIG. 4, with the period T of the periodic sequence of individual stimuli typically (and ideally) lying close to the mean period of pathological oscillation. For example, a literature value can be used for the mean period of pathological oscillation and it is possible to deviate from the literature value by e.g. up to ±5%, ±10% or ±20%.

The principle of the soft reset is based on the fact that an oscillation in accordance with so-called entrainment and the ending of the entraining stimulus sequence has a preferred phase difference from the entrained stimulus sequence. This can be detected the easiest in that a periodic sequence of e.g. 100 individual stimuli 35 is applied for the entrainment. the first 10 individual stimuli 35 are neglected to avoid possible transience and an entrainment index is calculated for the sequence of the remaining 90 individual stimuli 35. For this purpose the phase-locking index (from "Detection of n:m phase locking from noisy data: application to magnetoencephalography" by P. Tass et al.; published in Physical Review Letters, 1998, Volume 81, No. 15, pages 3291 to 3294) between the phase of the sequence of individual stimuli 35 (whose phase increases linearly by $2\pi$ within each period) and the phase, determined e.g. by means of Hilbert transformation, of the signal acquired by means of band pass filtering or empirical mode decomposition which represents the pathological synchronous neural activity. Alternatively, the phase locking index can also be calculated using the calculation of the amount of the circular mean value of all phase differences within the sequence of the remaining 90 individual stimuli 35. The phase locking index calculates how greatly the distribution of the phase differences within the sequence of the remaining 90 individual stimuli 35 differs from a uniform distribution. A relative entrainment is present when the phase locking index exceeds the 99th percentile (or twice or three times the 99th percentile) of the prestimulus distribution of the phase locking index. The prestimulus baseline of the phase locking index is calculated in that a surrogate sequence of 90 individual stimuli is used prior to the stimulus application to calculate a phase locking index for the spontaneous (i.e. uninfluenced by stimulation) pathological signal (that is to act as if an entrainment was taking place in order to see which values the phase locking index can randomly adopt). This calculation of the phase locking index is carried out e.g. in 100 prestimulus intervals (in each case having a length of 90 periods of the actually used individual stimuli). This provides a distribution which allows the extent of randomly high values of the phase locking index to be estimated.

If an entrainment is not possible in this manner, the total procedure can be restarted using a new start selection of the first stimuli 34 (e.g. another tone interval or another skin area).

Provided that all first stimuli 34 (or 35) from the start selection (whether determined by means of the phase resetting index or the entrainment index) have achieved a phase reset, the control and analysis unit 10 adds second stimuli from a second stimulus parameter range to the start selection of the first stimuli 34 (or 35) of the first stimulus parameter range in a second step. The second stimuli are so-called "marginal stimuli" which lie outside the first stimulus parameter range (e.g. tones outside the initial tone interval or localizations outside the initial visual field region or skin area). The second stimulus parameter range in particular comprises the first stimulus parameter range, i.e. the first stimulus parameter range is completely included in the second stimulus parameter range.

The second stimuli are also tested as described above as to whether they can reset the phase of the pathological, synchronized and oscillatory brain activity. If this is not possible, new second stimuli are selected.

The start selection hereby achieved should comprise the initial start selection of the first stimuli 34 (or 35) and furthermore also include further remote second stimuli in accordance with the tonotopic or somatotopic organization of the associated brain area. It is important for the selection of the effective, i.e. phase resetting, individual stimuli to determine the limits of the tone interval or of the visual field region or of the skin area to cover the brain zone having the pathological neural synchronization as completely as possible with the individual stimuli.

In accordance with an embodiment, the determination of the second stimuli only takes place when it is to be assumed with symptoms in accordance with the tonotopic or somatotopic organization of the associated affected brain area that only one circumscribed range of individual stimuli can be effective (or particularly effective).

A determination of the second stimuli is e.g. to be carried out in the cases shown below or is dispensable.

The acoustic CR stimulation for treating tinnitus is the most effective with individual stimuli of one pitch which are able to reset the phase of the pathological synchronous activity which is located in a circumscribed frequency range of the tonotopically arranged central auditory system. The determination of the second stimuli should be carried out here as described above.

The vibro-tactile CR stimulation, e.g. for treating locomotion disorders (Parkinson's, dystonia), pathological tremor, functional disorders after a stroke, chronic pain syndromes (also amputation pain) is the most effective with individual stimuli which are applied at skin localizations and which are able to reset the phase of the pathologically synchronous brain activity which is located in a circumscribed region of the somatotopically arranged central sensomotoric system. The determination of the second stimuli should be carried out here as described above.

With ADHS and obsessive compulsive disorders, the primary focus of the pathologically synchronous neural activity is not in primary sensory brain areas, e.g. in the auditory cortex or in the primary motor cortex. The CR stimulation is thus not to be restricted to a desynchronization of specific part regions of the associated primary sensory or motor brain areas. The desynchronizing effect of the CR stimulation is rather forwarded to the downstream brain areas which have pathologically synchronous neural activity and there develops its desynchronizing effect. The determination of the second stimuli can be dispensed with in diseases in which primary sensory or primary motor brain areas are not primarily affected by the pathological neural synchronization. In these cases it is, however, all the more important to test the effectiveness of the CR stimulation in accordance with the fourth step described further below in order e.g. to be able to preclude too small a scattering of the start values (which result in a desynchronization in too small a brain area and thus in a delayed CR effect).

The measured signals 23 recorded by the measuring unit 12 to carry out the calibration described here are e.g. either analyzed directly after a corresponding preprocessing (e.g. after the elimination of artifacts such as blinking artifacts familiar to the skilled person) by means of EEG or MEG signals or after determining the underlying brainwaves by means of processes known to the skilled person for the backward calculation (using spatially distributed current densities or a plurality of dipoles). In the latter case, the temporal pattern of brainwaves or dipolar moments is analyzed. This allows a calibration to be carried out which is specifically adapted to the phase resetting effect in one or more particularly relevant brain areas (e.g. in the primary auditory cortex in acoustic CR neuromodulation for treating tinnitus).

If the region of the effective, i.e. phase resetting, first stimuli 34 and possible second stimuli is not contiguous, but contains "holes" (e.g. a tone can be ineffective, i.e. cannot effect any phase reset in the middle of the interval of effective tones), the different effective (phase resetting) regions (e.g. tone intervals) are determined via a finer resolution of the start values of the first stimuli 34. A group of individual stimuli effective for the CR stimulation can then be determined separately for the treatment as described above and in the following for each effective region (e.g. each effective tone interval). Combined CR tone sequences can, however, also be used for the treatment.

Once the selection of the effective, i.e. phase resetting, first and possibly second individual stimuli has been carried out in the above-described first two steps, the control and analysis unit 10 determines those individual stimuli (called third stimuli 38 in the following) in a third step which stimulate the associated brain area as equidistantly as possible to avoid the same subpopulation being stimulated over a plurality of channels, which could result in an excitation of the synchronous activity. This is estimated by the following functional criterion. In addition to the outwardly disposed first or second stimuli (e.g. the highest and lowest phase resetting tones) in accordance with the physiological scaling familiar to the skilled person (e.g. logarithmic tonotopic scale) and in accordance with medical practicability (e.g. in the positioning of vibro-tactile stimulators or thermostimulators), a few further third stimuli 38 are selected, disposed in the effective region and distributed over the total range of the effective first and possibly second stimuli.

Figure 5:
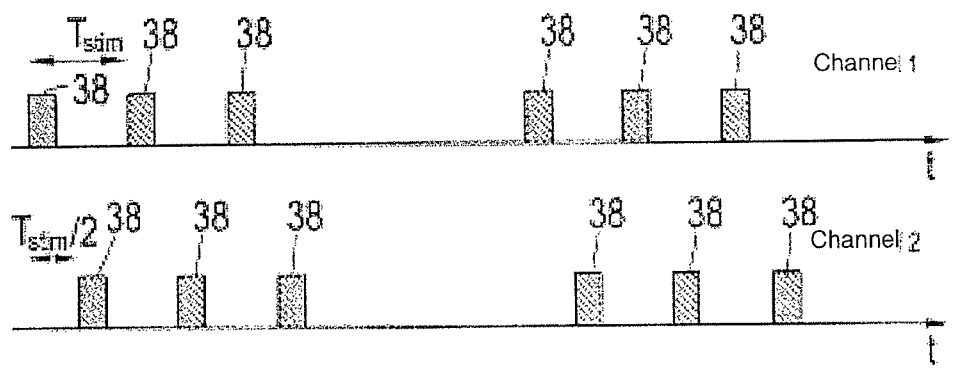
FIG. 5 a schematic representation of CR neuromodulation having two adjacent stimuli in accordance with tonotopy or somatotopy.

FIG. 5 schematically shows a CR stimulation which is carried out with two third stimuli 38 which are adjacent in accordance with the tonotopy or somatotopy, with one channel corresponding to each of the two third stimuli 38 used. The respective third stimulus 38 in a sequence is periodically applied with the period $T_{stim}$ in each of the two channels. In the present case, each sequence comprises three third stimuli 38; however, the sequences can also include further third stimuli 38. A pause is observed after each sequence and the sequence is then repeated. The time delay between the sequences of different passages furthermore amounts to $T_{stim}/2$.

The period $T_{stim}$ is selected close to the mean period of the pathological oscillation. For example, the stimulation frequency $f_{stim}=1/T_{stim}$ is either adapted to the frequency band to be desynchronized (e.g. with a pathological synchronization in the delta band a stimulation frequency located therein or, even better, a simulation frequency located in the lower half, that is e.g. 1.5 Hz) or—e.g. before the start of each test (of the respective stimuli) quasi online—adapted to the peak in the power spectrum of the pathological frequency band. In the latter case, the stimulation frequency $f_{stim}$ is selected such that it corresponds to 1:1 of the peak frequency or to a smaller n:m multiple thereof (if the stimulation frequency would otherwise be too high, e.g. above 2. Hz, and thus would be psychoacoustically too unpleasant) (n, m are whole numbers). Furthermore, a literature value for the mean period of the pathological oscillation can be used and the period $T_{stim}$ used for the stimulation can differ from this literature value by e.g. up to ±5%, ±10% or ±20%. The stimulation frequency $f_{stim}$ typically lies in the range from 1 to 30 Hz.

The third stimuli 38 are selected as functionally good if combinations of two third stimuli 38 adjacent in accordance with tonotopy of somatotopy applied as CR stimulation have the effect that no amplitude increase of the pathological oscillations (that is no reinforcement of the synchronization of the pathologically synchronized neural population generating the signal) or even a light decrease occurs (corresponds to a weak desynchronization). If this is not the case with a pair, the (tonotopic or somatotopic) distance between the two third stimuli 38 has to be increased, e.g. in that the inner individual stimulus is displaced from the outer individual stimulus. This test then has to be carried out again for the respective adjacent further adjacent individual stimuli. The third step is applied to all pairs of tonotopically or somatotopically adjacent individual stimuli until the third stimuli 38 are found of which respectively all tonotopically or somatotopically adjacent individual stimulus pairs applied as CR stimulation do not effect any amplitude increase in the pathological oscillation.

Figure 6:
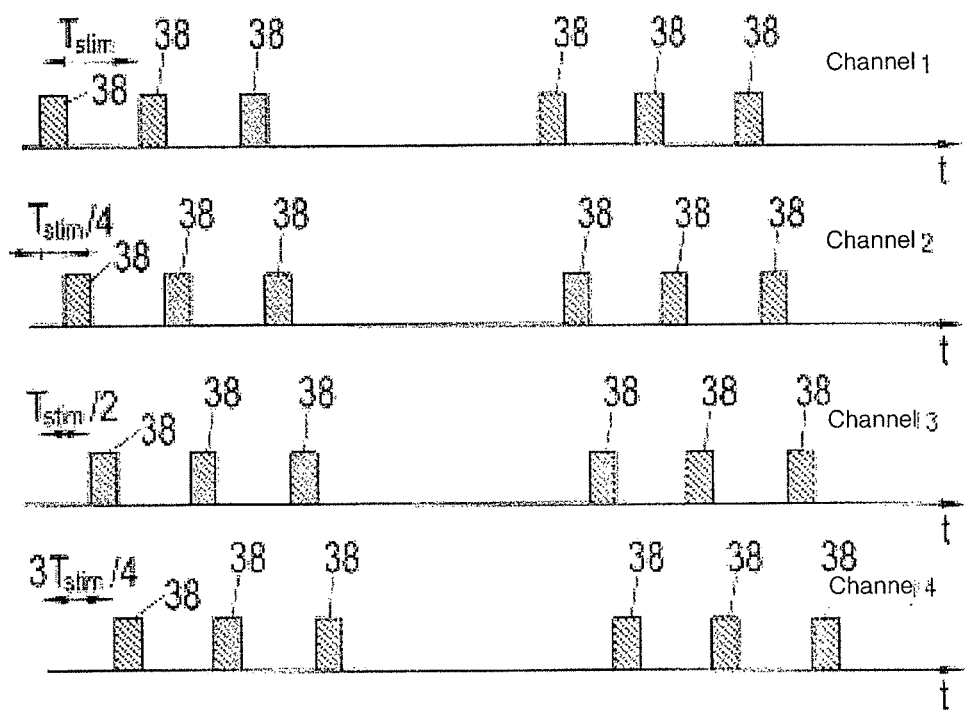
FIG. 6 a schematic representation of CR neuromodulation with four stimuli.

In a fourth step, the control and analysis unit 10 checks whether the associated CR stimulation suppresses the pathologically synchronous and oscillatory neural activity of the stimulated neurons and in particular has a desynchronizing effect on a use of all third stimuli 38 determined in the third step. FIG. 6 shows an example with four third stimuli 38 in total, i.e. four channels. In each of the four channels, the respective third stimulus 38 in a sequences is applied periodically with the period $T_{stim}$, where $T_{stim}$ is here also close to the middle period of the pathological oscillation or deviates from the literature value by up to ±5%, ±10% or ±20% (typically $f_{stim}=1/T_{stim}$ lies in the range from 1 to 30 Hz. In the present example, each sequence comprises three third stimuli 38; however, the sequences can also include more third stimuli 38. A specific pause is observed after each sequence and the sequence is then repeated. The time delay between the sequences of adjacent channels furthermore amounts to $T_{stim}/4$, since four channels are present. For the general case of N channels, the time delay of adjacent channels would amount to $T_{stim}/N$.

A CR stimulation as shown in FIG. 6 with all selected third stimuli 38 should result in a reduction in the amplitude of the pathological signal, which corresponds to a CR-induced desynchronization of the underlying, pathologically synchronized neural population. If this is not the case, the total procedure can be carried out again with another start selection of the first stimuli 34.

A typical (applicative) error in the handling of the apparatus 1 is too small a selected start selection. E.g. only a small tone interval or only a small skin area is selected. The pathological synchronous neural process is, however, considerably more extended so that only a small portion of the affected neural population can be stimulated with the selection of individual stimuli which is too small in accordance with the tonotopy or somatotopy and thus the total population cannot be desynchronized efficiently and fast.

The individual stimuli used in the above calibration procedure should have a strength close to the perception threshold known to the skilled person, e.g. the stimulus strength in the acoustic stimulation can only lie a few dB (e.g. 5 dB) above the auditory threshold. The stimuli can, however, also be selected as stronger. Furthermore, the ideal stimulus strength (stimulus intensity) can be calibrated with the apparatus 1. It should naturally always lie in an intensity range pleasant for the patient; stimulus intensities potentially harmful to the health should be avoided.

After a successful calibration, the therapy can be carried out using CR neuromodulation. In this respect, different kinds of CR stimulation can be used. In an "N from N" CR stimulation, all N different individual stimuli are applied per stimulation cycle as in FIG. 4 (for N=4). Alternatively, an "M from N" CR stimulation (M<N) can be used, i.e. M, e.g. different individual stimuli are selected and applied in a randomized manner from N different individual stimuli per stimulation cycle. In this manner, the psychophysical impression of the stimulation can be varied by a larger selection of individual stimuli. I.e. acoustic CR stimulation sequences can in this manner sound more complex so that it is possible to obviate the possible impression of monotony in the patient.

The conventional subjective measurement (e.g. audiometric adaptation with acoustic CR stimulation) or clinical testing (e.g. with vibro-tactile stimulation or thermostimulation) can be replaced by an objective examination to be carried out systematically thanks to the apparatus 1. The latter makes it possible to replace the measurement of subjective impressions of the patient or of subjective impressions of the physician or medical assistants making the evaluation with an electrophysiologically based measurement of the stimulus responses of the brain for calibrating the ideal stimulation parameters and stimulation sites.

Stimulation Units for Generating Acoustic Stimuli:

In the following, embodiments of the non-invasive stimulation unit 11 for generating acoustic stimuli 22 are described (the stimuli 22 comprise the first, second and third stimuli). Such stimulation units can also be seen from German patent applications No. 10 2008 015 259.5 having the title "Apparatus and method for auditory stimulation" which was deposited at the German Patent and Trademark Office on Mar. 20, 2008. The total disclosure content of German patent application No. 10 2008 015 259.5 is herewith included in the disclosure of the present application.

The frequency spectrum of the acoustic stimuli can lie completely or partly in the range audible for humans. The acoustic stimuli preferably have, for example, the four pure tones shown in FIG. 7 having the frequencies $f_1$, $f_2$, $f_3$ and $f_4$ for the treatment of patients having tonal tinnitus (or also for treating patients with hissing tinnitus). The acoustic stimuli are received by the patient via one or both ears, are converted into nerve impulses in the inner ear and are forwarded via the auditory nerve or nerves to neural populations in the brain. The acoustic stimuli are designed such that they stimulate neural populations in the auditory cortex. A specific part of the auditory cortex is activated by the tonotopic arrangement of the auditory cortex on the acoustic stimulation of the inner ear at a specific frequency. The tonotopic arrangement of the auditory cortex is described e.g. in the following articles: "Tonotopic organization of the human auditory cortex as detected by BOLD-FMRI" by D. Bilecen, K. Scheffler, N. Schmid, K. Tschopp and J. Seelig (published in Hearing Research 126, 1998, pages 19 to 27), "Representation of lateralization and tonotopy in primary versus secondary human auditory cortex" by D. R. M. Langers, W. H. Backes and P. van Dijk (published in NeuroImage 34, 2007, pages 264 to 273) and "Reorganization of auditory cortex in tinnitus" by W. Mühlnickel, T. Elbert, E. Taub and H. Flor (published in Proc. Natl. Acad. Sci. USA 95, 1998, pages 10340 to 10343).

On a CR stimulation, the acoustic stimuli are designed such that, for example, the neural population 27 of the auditory cortex shown schematically in FIG. 1 is stimulated by a pathologically synchronous and oscillatory activity. The neural population 27 can be subdivided into different subpopulations, inter alia into the subpopulations 28 to 31 shown in FIG. 1, at least mentally before the start of the stimulation. The neurons of all subpopulations 28 to 31 fire largely synchronously and on average at the same pathological frequency before the start of the stimulation. Due to the tonotopic organization of the auditory cortex, the subpopulation 28 is stimulated by means of the frequency $f_1$, the subpopulation 29 by means of the frequency $f_2$, the subpopulation 30 by means of the frequency $f_3$ and the subpopulation 31 by means of the frequency $f_4$. The stimulation by the acoustic stimuli effects a reset of the phase of the neural activity of the stimulated neurons in the respective subpopulations 28 to 31.

Due to the tonotopic arrangement of the auditory cortex and to the plurality of frequencies $f_1$ to $f_4$, which are contained in the acoustic stimuli, it is possible to stimulate the pathological neural population 27 directly at the different sites 28 to 31. This makes it possible to reset the phase of neural activity of the pathological neural population 27 at the different simulation sites 28 to 31 at different points in time in that the frequencies $f_1$ to $f_4$ are applied at different points in time. As a result, the pathological neural population 27 whose neurons were previously active synchronously and at the same frequency and phase are split into the subpopulations 28 to 31. The neurons are still synchronous within each of the subpopulations 28 to 31 and also still fire on average at the same pathological frequency, but each of the subpopulations 28 to 31 has the phase with respect to their neural activity which was forced on it by the stimulation stimulus having the associated frequency $f_1$ to $f_4$.

Due to the pathological interaction between the neurons, the state with a plurality of subpopulations 28 to 31 generated by the stimulation is unstable and the total neural population 27 fast approaches a state of complete desynchronization in which the neurons fire without correlation.

To stimulate the auditory cortex focally at different sites, pure tones of the associated frequencies $f_1$, $f_2$, $f_3$ and $f_4$ have to be administered. As a consequence of the tonotopic arrangement of the auditory cortex, different parts of the brain are stimulated by the simultaneous administration of the associated different pure tones $f_1$ to $f_4$, i.e. by the superposition of different sinusoidal oscillations. If the four different sites 28 to 31 are e.g. stimulated at different times, the four different frequencies $f_1$ to $f_4$ are applied at the respective times. This is shown by way of example in FIG. 7. Sinusoidal oscillations having the frequencies $f_1$=1000 Hz, $f_2$=800 Hz, $f_3$=600 Hz and $f_4$=400 Hz are here applied successively and in pulse form, which results in a successive focal stimulation at the four different sites 28 to 31 of the auditory cortex. The strength of the stimulation of the respective area in the auditory cortex generated by the respective sinusoidal oscillation corresponds to the amplitude of the respective sinusoidal oscillation.

Figure 7:
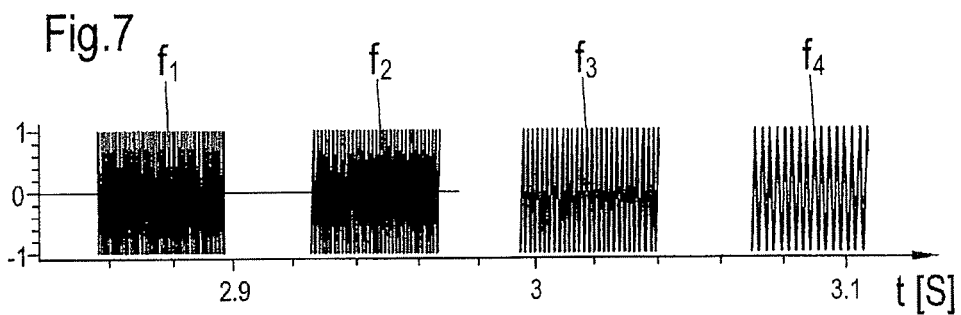
FIG. 7 a representation of sinusoidal oscillations at different frequencies.
Figure 8A:
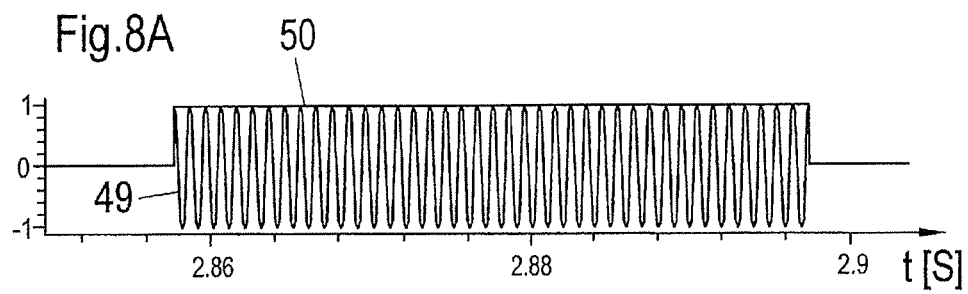
FIGS. 8A and 8B schematic representations of different tones and tone packets.

The generation of the pulse-like sinusoidal oscillations shown in FIG. 7 is represented by way of example in FIG. 8A. A sinusoidal oscillation 49 having a rectangular function 50 which can adopt the values 0 or 1, for example, is multiplied there. At the times at which the rectangular function 50 has the value 0, the associated stimulus is switched off and during the time in which the rectangular function 50 is equal to 1, the stimulus is switched on.

Instead of the rectangular function 50, the sinusoidal oscillation 49 can be multiplied by any desired other function. As a result, this multiplication corresponds to an amplitude modulation of the sinusoidal oscillation 49.

To avoid click noises due to an abrupt start and end of the tones, a smoother course can be selected instead of the rectangular function 50, e.g. by multiplication of the sinusoidal oscillation 49 by a sinusoidal half-oscillation of a suitable duration, e.g. the duration of a stimulus.

Instead of the above-described sinusoidal oscillations, oscillating signals can also be used for generating the acoustic stimuli having a different signal shape such as rectangular signals which oscillate at the corresponding base frequency.

If a less focal stimulation is preferred instead of a focal stimulation that activates larger parts of the auditory cortex, frequency mixtures instead of individual frequencies are applied, for example in pulse shape. By means of a frequency mixture in the borders between a lower frequency $f_{lower}$ and a higher frequency $f_{upper}$, all those parts of the auditory cortex are stimulated which are stimulated by the frequencies between $f_{lower}$ and $f_{upper}$ due to the tonotopic arrangement. If e.g. four different larger regions of the auditory cortex should be stimulated at different times, the four associated frequency mixtures having the borders $f_{j,lower}$ and $f_{j,upper}$ (j=1, 2, 3, 4) are applied at the desired times.

To treat patients having hissing tinnitus, tone packages having the respective frequency distributions $v_1$, $v_2$, $v_3$ and $v_4$ with an absolute width (in Hz) or a relative width (i.e. standardized with respect to the middle frequency or the frequency of maximum power) can be used instead of the four pure tones having the frequencies $f_1$, $f_2$, $f_3$ and $f_4$. Examples for such frequency distributions $v_1$, $v_2$, $v_3$ and $v_4$ can be found in FIG. 8B.

Figure 8B:
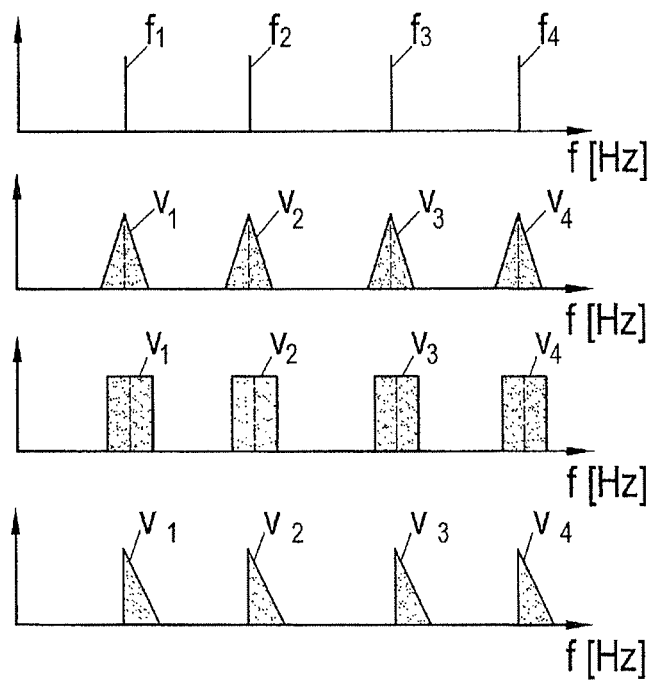

The topmost partial image shows the pure tones $f_1$, $f_2$, $f_3$ and $f_4$ predominantly used in patients with tonal tinnitus. In patients with hissing tinnitus, tone packages can also be used. In this respect, they can be distributions symmetrical with respect to a middle frequency (second and third part images from above) or also asymmetric distributions (lowest part image). The distributions can, as shown in FIG. 8B, have edges or smooth curves. The phases of the frequencies of the individual distribution $v_j$ can be randomized using different noise processes familiar to the skilled person. The phases of the individual frequencies can in this respect be alternately uncorrelated or have correlations familiar to the skilled person (e.g. dropping exponentially with the frequency difference). The phases in the different frequency distributions $v_1$, $v_2$, $v_3$ and $v_4$ can also be correlated with one another or can be independent of one another. E.g. the same noise process can determine the phases of the individual frequencies in all frequency distributions $v_1$, $v_2$, $v_3$ and $v_4$. Both the phases of the individual frequencies and the frequency distributions can, however, also be determined in that a repertoire of different frequency distributions and phase distributions (e.g. different noise processes) is offered to the patient and the frequency distribution and phase distribution is selected whose sound characteristic is most similar to the ear noise of the patient.

An acoustic CR stimulation will be explained by way of example in the following with reference to the four pure tones having the frequencies $f_1$ to $f_4$ in which CR stimulation a desynchronization of the total neural population can be achieved by time-offset resetting of the phase of the neural activity of subpopulations of a pathologically synchronous and oscillatory neural population. The four frequencies $f_1$ to $f_4$ are only to be understood by way of example, i.e. any other desired number of frequencies or frequency mixtures can be used for stimulation purposes. For example, the CR stimulation can be carried out using the tone packages shown in FIG. 8B and having the frequency distributions $v_1$ to $v_4$ instead of the four pure tones having the frequencies $f_1$ to $f_4$.

Figure 9A:
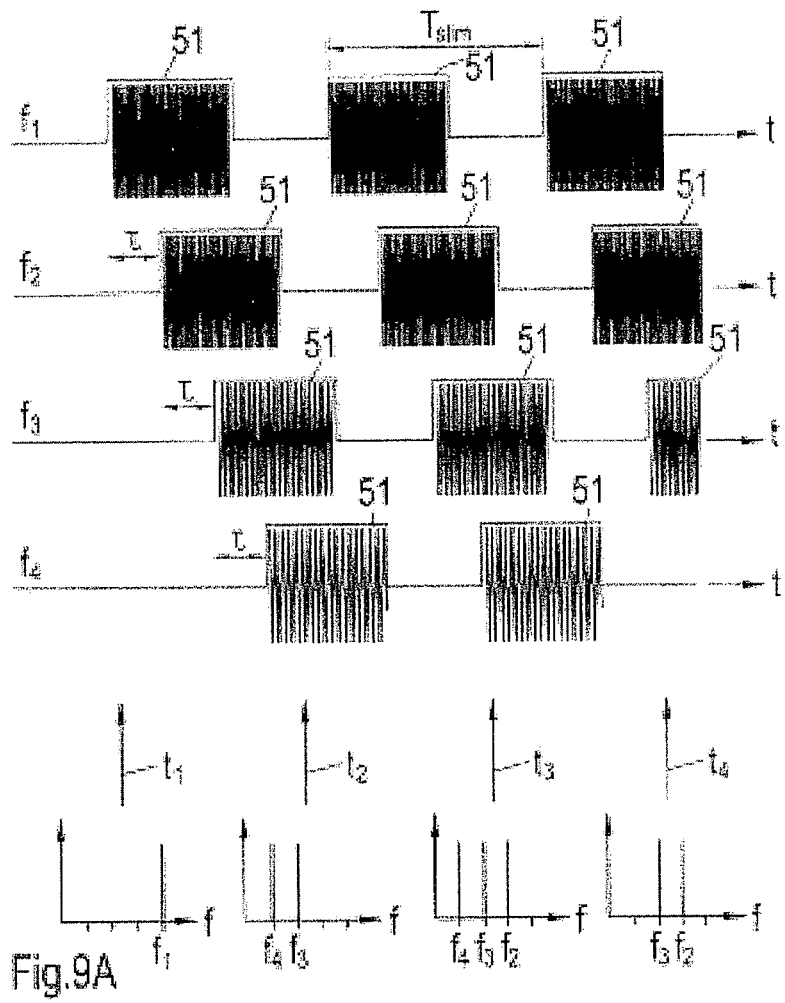
FIGS. 9A and 9B schematic representations of different acoustic CR neuromodulations.

A stimulation method suitable for the above-described purposes is shown schematically in FIG. 9A. In FIG. 9A, four sinusoidal oscillations having the frequencies $f_1$, $f_2$, $f_3$ and $f_4$ are applied below one another in the top four lines against the time t, i.e. each line corresponds to one of the channels from FIG. 6. Acoustic stimuli 51 are formed from the sinusoidal oscillations shown. To generate pulse-shaped sinusoidal oscillations, the four sinusoidal oscillations have been multiplied by rectangular functions. Each sinusoidal oscillation pulse is repeated periodically with a frequency $f_{stim}$. The frequency $f_{stim}=1/T_{stim}$ can lie in the range from 1 to 30 Hz and in particular in the range from 1 to 20 Hz, but can also adopt smaller or larger values. Such sequences of pulse-shaped sinusoidal oscillations are suitable, when they are applied as acoustic stimuli 51, to reset the neural phase of the respective stimulated pathological neural subpopulation 28 to 31. The phase reset in this respect does not necessarily already result after one phase or a few phases, but a certain number of the sinusoidal oscillation pulses 51 shown in FIG. 9A may be necessary to reset the neural phase of the respective subpopulation 28 to 31.

The frequency $f_{stim}$ can lie, for example, in the range of the mean frequency of the pathologically rhythmic activity of the target network. With neurological and psychiatric diseases, the mean frequency is typically in the range from 1 to 30 Hz, but can also lie outside this range. With tinnitus, excessively synchronous neural activity is found e.g. in the frequency range from 1.5 to 4 Hz. It must be noted in this respect that the frequency at which the pathological neurons fire is usually not constant, but can rather have variations and furthermore shows individual deviations in each patient.

To determine the frequency $f_{stim}$, for example, the mean peak frequency of the pathological rhythmic activity of the patent can be determined by means of EEG or MEG measurements. This peak frequency can then be used as the stimulation frequency $f_{stim}$ or can also be varied, for example in a range from $f_{stim}-3$ Hz to $f_{stim}+3$ Hz.

The duration of a sinusoidal oscillation pulse 51, i.e. the time duration in which the rectangular function adopts the value 1 in the present embodiment, can amount to $T_{stim}/2$ for example. In this case, the time duration during which the respective frequency contributes to the stimulation and the subsequent stimulation pause are of equal length. It is, however, also possible to select other stimulation durations, for example in the range of $T_{stim}/2-T_{stim}/10$ to $T_{stim}/2+T_{stim}/10$. The stimulation durations can, for example, be determined experimentally.

In accordance with the embodiment shown in FIG. 9A, the administration of the individual frequencies $f_1$ to $f_4$ takes place with a time delay between the individual frequencies $f_1$ to $f_4$. For example, the start of pulses following one another in time and having different frequencies can be displaced by a time τ.

In the case of N frequencies which are used for stimulation, the time delay τ can lie between respective mutually following pulses, for example in the range of an Nth of the period $T_{stim}=1/f$. In the embodiment (N=4) shown in FIG. 9A, the time delay τ accordingly amounts to $T_{stim}/4$. It is possible to deviate up to a specific degree from the requirement that the time delay τ between two respective mutually following sinusoidal oscillation pulses amounts to $T_{stim}/N$. For example, it is possible to deviate from the value $T_{stim}/N$ for the time delay τ by up to ±5%, ±10% or ±20%. On such a deviation, stimulation successes were still achieved, i.e. a desynchronizing effect could still be observed.

The acoustic stimulus is formed by superposition from the periodic sinusoidal oscillation pulses 51 having the frequencies $f_1$ to $f_4$. The individual sinusoidal oscillation pulses 51 can in this respect be combined with one another, for example, in a linear or non-linear manner. This means that the sinusoidal oscillations of the individual frequencies $f_1$ to $f_4$ do not necessarily have to be combined with the same amplitudes to form the acoustic stimulus. The frequency spectrum of the acoustic stimulus is shown by way of example at four different points in time $t_1$, $t_2$, $t_3$ and $t_4$ in the bottommost line of FIG. 9A. The frequency spectra shown there, in particular the height and shape of the frequency peaks, are only to be understood by way of example and can also have completely different shapes. The following statements can be taken in detail from the frequency spectra shown: At the time $t_1$, only the frequency $f_1$ appears in the acoustic stimulus. At the time $t_2$, the frequencies are $f_3$ and $f_4$; at the time $t_3$, the frequencies are $f_2$ to $f_4$; and at the time $t_4$, the frequencies are $f_2$ and $f_3$.

In accordance with an alternative embodiment, four frequency mixtures having the boundaries $f_{j,lower}$ and $f_{j,upper}$ (j=1, 2, 3, 4) are used instead of the frequencies $f_1$ to $f_4$. In a frequency mixture j, any desired number of frequencies can be present in the range from $f_{j,lower}$ to $f_{j,upper}$. A further alternative is represented by the tone packages shown in FIG. 8B and having the frequency distributions $v_1$ to $v_4$.

Figure 9B:
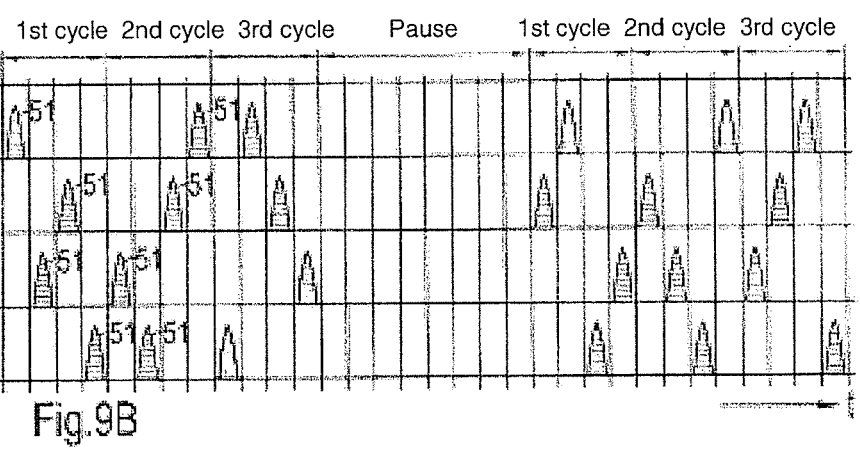

Further variations of the acoustic CR stimulation are shown in FIG. 9B. Since contours having sharp edges such as the rectangular functions shown in FIGS. 8A and 9A result in click noises, a smoother curve is selected in practice. A CR stimulation having sinusoidal oscillation pulses 51 whose contour is a cosine half wave is shown as an example for this in FIG. 9B.

Furthermore FIG. 9B shows a deviation from the strictly periodic stimulation pattern of FIG. 9A. The order in which the stimuli 51 are applied has been randomized per cycle in FIG. 9B. In addition, a pause is provided during which no stimulation takes place. Such pauses can be selected to be of any length and can in particular amount to a whole-number multiple of the cycle duration.

Figure 10:
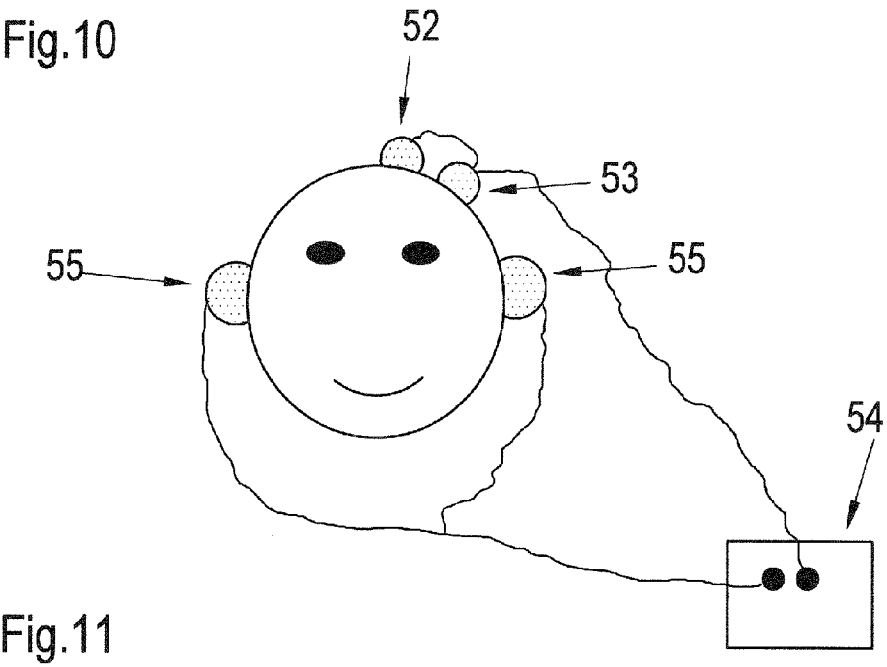
FIG. 10 a schematic representation of an apparatus for acoustic desynchronizing neurostimulation.

FIG. 10 schematically shows an apparatus for the EEG-based calibration of the CR tones for the treatment of neurological and psychiatric diseases, e.g. tinnitus, ADHS, OCD. Non-invasively fixed EEG electrodes 52, 53, which are connected via a cable, serve as a measuring unit and measure the EEC stimulus responses which are passed on over a cable to the central control and analysis unit 54. Acoustic test stimuli are administered to the patient via earphones or headphones 55. The control signals used for this purpose are generated by the control and analysis unit 54 and are used for the data analysis of the EEC stimulus responses.

In the following, the calibration already described generally above for the determination of the ideal stimulus parameter will be explained with respect to acoustic CR neuromodulation. A flowchart to illustrate the procedure of the calibration for the acoustic CR neuromodulation is shown in FIG. 11.

In the first step, first stimuli 56 are generated and administered to the patient with the aid of the earphone or headphone 55 (or generally the stimulation unit). In the case of a tinnitus treatment, tones in a first frequency interval about the dominant tinnitus frequency of the patient (with tonal tinnitus) can be selected as a start selection as first stimuli 56, for example. The first frequency interval can be covered with the first stimuli 56 in accordance with the physiological mapping characteristics (e.g. in a first approximation logarithmic tonotopic map in the primary auditory cortex) familiar to the skilled person such that these first stimuli cover the respective cortical representation equidistantly in a first approximation, i.e. the associated target sites in the brain which are stimulated by the first stimuli should have the same spatial distances from one another, that is should be equidistant, in a first approximation.

The first stimuli 56 are tested by the control and analysis unit 54 as to whether they can reset the phase of the pathological, synchronized and oscillatory brain activity. In this respect, those first stimuli 56 are selected from the preselection of first stimuli 56 which can reset the phase of the pathological, synchronized and oscillatory brain activity. FIG. 11 shows by way of example the first stimuli 56 selected in this respect in step 2. The non-effective, i.e. non-phase resetting and accordingly discarded, first stimuli 56 are shown dashed in step 2.

Figure 11:
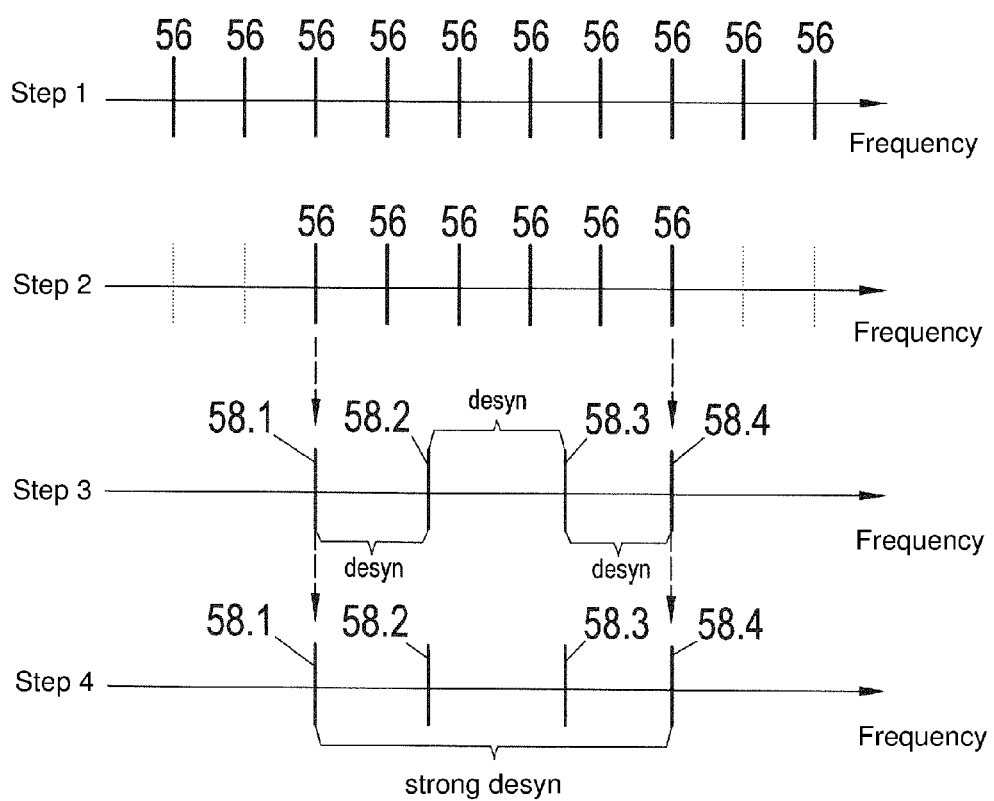
FIG. 11 a flowchart for illustrating the calibration of the apparatus shown in FIG. 10.

Provided that all first stimuli 56 from the start selection, i.e. all the first stimuli 56 shown in step 1 of FIG. 11, are able to reset the phase of the pathological, synchronized and oscillatory brain activity, second stimuli ("marginal stimuli" not shown in FIG. 11) are added to these first stimuli 56. The second stimuli are tones which are disposed outside the first frequency interval. The second stimuli are disposed outside a second frequency interval which comprises the first frequency interval. Those stimuli are also selected from among the second stimuli which can reset the phase of the pathological, synchronized and oscillatory brain activity.

Once the effective, i.e. phase resetting, tones have been selected in the second step, the control and analysis unit 54 determines those third stimuli 58 in the third step which stimulate the associated area of the brain as equidistantly as possible. The procedure is as follows for this purpose. In the event that no second stimuli were selected in the second step, a few further stimuli are selected distributed over the total effective frequency range beside the outwardly disposed first stimuli 56 (i.e. the highest and lowest phase resetting tones) in accordance with the physiological scaling familiar to the skilled person (e.g. logarithmic tonotopic scale), the frequency of said stimuli lying between the two outwardly disposed effective first stimuli 56. These stimuli form the third stimuli 58. Four third stimuli 58.1, 58.2, 58.3 and 58.4 are shown by way of example in FIG. 10. The target sites of the third stimuli 58.1 to 58.4 are preferably approximately equidistant in the brain or spinal cord of the patient. The number of the third stimuli 58.1 to 58.4 is typically smaller than the number of the first stimuli 56 selected in the second step.

If second stimuli were selected in the second step, the second stimuli disposed outwardly in the effective (second) frequency range are selected as "marginal stimuli" of the third stimuli 58 (corresponding to the stimuli 58.1 and 58.4 from FIG. 11). Still further third stimuli (corresponding to the stimuli 58.2 and 58.3 from FIG. 11) are distributed between these outer second stimuli. The number of third stimuli is here also preferably smaller than the number of the effective first and second stimuli.

A CR stimulation such as is shown in FIG. 9A (in this case with only two channels) is respectively carried out pair-wise with the third stimuli 58.1 to 58.4. The stimulus pair 58.1/58.2 is first tested. If this test results in an amplitude increase of the pathological oscillation (that is a in a reinforcement of the synchronization of the pathologically synchronized neural population generating the signal), the stimulus 58.2 is displaced for so long toward higher frequencies until the CR stimulation with the stimulus pair 58.1/58.2 no longer shows any amplitude increase in the pathological oscillation. The stimulus pair 58.2/58.3 is subsequently tested in the same way. If necessary, the stimulus 58.3 is here displaced toward higher frequencies until the amplitude of the pathological oscillation no longer increases in the CR stimulation. The stimulus pair 58.3/58.4 is then tested in the same way. It can occur in this respect that the outermost stimulus 58.4 migrates out of the second frequency interval. In this case, the stimulus 58.4 or another stimulus, e.g. the stimulus 58.3, can optionally be discarded. In the latter case, the test would be carried out again using the stimulus pair 58.2/58.4.

In the fourth step, the control and analysis unit 54 checks whether the CR stimulation suppresses the pathologically synchronous and oscillatory neural activity of the stimulated neurons and in particular has a desynchronizing effect on the use of all third stimuli 58.1 to 58.4 determined in the third step. For this purpose, a CR stimulation is carried out such as is shown in FIG. 9A. Such a CR stimulation with all selected third stimuli 58.1 to 58.4 should produce a fall in the amplitude of the pathological signal, which corresponds to a CR-induced desynchronization of the underlying pathologically synchronized neural population.

Stimulation Units for Generating Optical Stimuli:

In the following, embodiments of the non-invasive stimulation unit 11 for generating optical stimuli 22 will be described. Such stimulation units can also be seen from the German patent application No. 10 2008 012 669.1 having the title "Apparatus and method for visual stimulation" which was filed with the German Patent and Trademark Office on Mar. 5, 2008. The total disclosure content of German patent application No. 10 2008 012 669.1 is herewith included in the disclosure of the present application.

Figure 12:
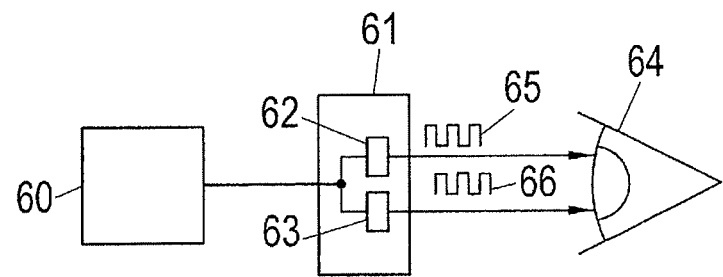
FIG. 12 a schematic representation of an apparatus for optical desynchronizing neuro stimulation.

FIG. 12 schematically shows a control and analysis unit 60 and a stimulation unit 61 controlled by the control and analysis unit 60 (the measuring unit is not shown in FIG. 12). The stimulation unit 61 includes a plurality of stimulation elements for generating optical stimuli. In the present embodiment, the stimulation unit 61 has two stimulation elements 62 and 63 which are controlled by the control and analysis unit 60. An eye 64 of a patient is furthermore shown in FIG. 12.

During the operation of the stimulation unit 61, the stimulation elements 62 and 63 generate optical stimuli 65 or 66 which are perceived by the patient via one or both eyes 65 and are forwarded via the optic nerves to neural populations in the brain.

The optical stimuli 65, 66 can have an underlying luminosity variation or brightness variation (or variation of the light intensity or luminosity); for example, they can be applied as pulses or as sequences of pulses with varied luminosity or brightness. The optical stimuli 65, 66 can be administered in dependence on the embodiment of the stimulation unit 61 as a luminosity modulation of natural optical stimuli, e.g. by means of homogeneous or segmented transmission glasses, as a modulated optical stimulus occurring in addition to a natural optical stimulus, e.g. by means of partially transparent light glasses or as an artificial optical brightness stimulus, e.g. by means of non-transparent light glasses. If the patient perceives the optical stimuli 65, 66 via both eyes 64, the respective optical stimuli 65, 66 of both eyes 64 can be correlated or coordinated.

The optical stimuli 65, 66 generated by the stimulation elements 62, 63 can be designed such that when they are perceived by the retina and conducted via the optic nerve to a neural population having a pathologically synchronous and oscillatory activity, they effect a reset of the phase of neural activity of the stimulated neurons in the neural population.

Figure 13:
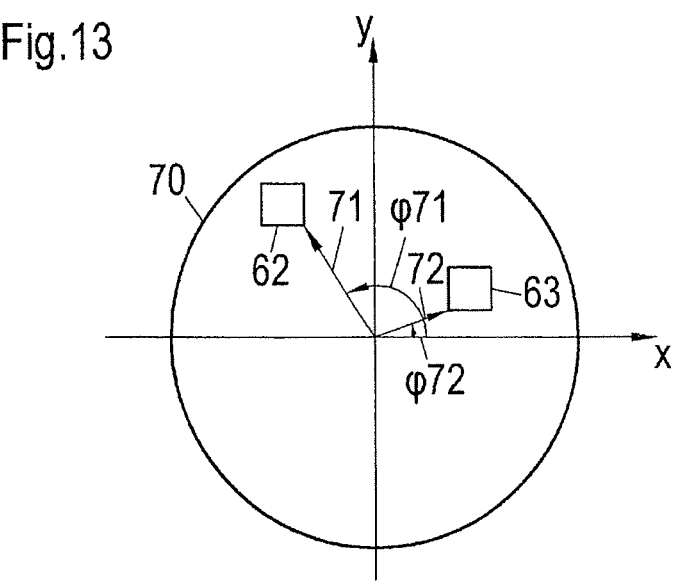
FIG. 13 a schematic representation of the visual field of a patient.

The visual field 70 of a patient is shown schematically in FIG. 13. That space is called the visual field which an eye can view without eye movements. The visual field 70 is shown as circular for reasons of simplicity in FIG. 13. The visual field typically has a more arched oval shape. The exact size and shape of the visual field is in this respect subject to individual fluctuations and is moreover age-dependent.

Points in the visual field 70 can be described, for example, with the aid of their polar coordinates. The spatial positions of the stimulation elements 62 and 63 are shown by way of example in the visual field 70 in FIG. 13. For illustration, a respective corner point of the stimulation elements 62 and 63 is marked with a vector 71 and 72 respectively. The vectors 71 and 72 can be described in the polar coordinate system via their amount and the angle $\phi_{71}$ or $\phi_{72}$ they include with the x axis.

Different points in the visual field 70 are imaged at different points of the retina via the crystalline lens of the eye. The different points of the retina are in turn connected via the optic nerve to different neurons in the brain. This means that respectively different neurons can be stimulated by the stimulation elements 62 and 63 arranged at different spatial locations. Consequently, the stimulation elements 62 and 63 as well as possibly further stimulation elements can be arranged spatially in the visual field 70 of the patient such that the optical stimuli perceived by the retina are forwarded to different target zones in the brain. Accordingly, different subpopulations of a pathological neural population can be directly stimulated by the stimulation elements 62 and 63 and a time-offset reset of the phases of this subpopulation can be carried out.

The association of the regions of the visual field with corresponding regions of the brain is described, for example, in the article "Visual Field Maps in Human Cortex" by B. A. Wandell, S. O. Dumoulin and A. A. Brewer, published in Neuron 56, October 2007, pages 366 to 383.

Figure 14:
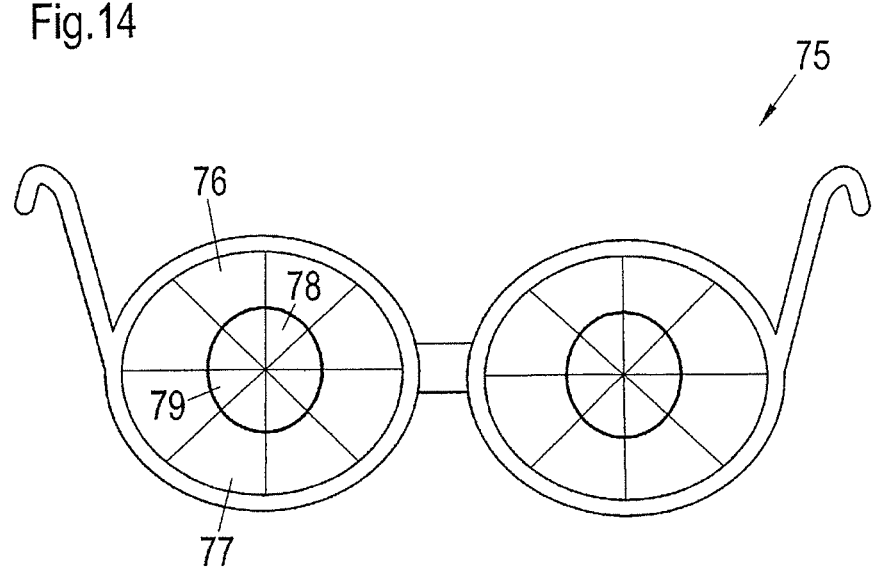
FIG. 14 a schematic representation of transmission glasses.

An embodiment of the stimulation unit 61 is shown schematically in FIG. 14 as transmission glasses 75 with segmented transmission lenses. The transmission lenses are each divided into different segments whose transmission can be controlled separately. The segmentation can, for example, be radial and/or circular (both are shown in FIG. 14). The transmission glasses 75 shown in FIG. 14 are only to be understood in an exemplary manner. The number of segments and the geometrical shapes of the individual segments can be selected differently.

The segments of the transmission glasses 75 correspond to the stimulation elements shown in FIG. 12. Four of the segments are marked by the reference numerals 76, 77, 78 and 79 by way of example in FIG. 14.

It will be explained by way of example in the following with reference to the segments 76 to 79 how a desynchronization of the total neural population can be achieved by means of a CR neuromodulation, that is by time-offset resetting of the phases of subpopulations of a pathologically synchronous and oscillatory neural population. The segments 76 to 79 have been selected such that the optical stimuli generated by them are each preferably perceived by a specific part of the retina of the patient from where the stimuli are forwarded to specific regions of the brain so that the above-described splitting of a pathological neural population into subpopulations is made possible (cf. e.g. neural populations 27 with subpopulations 28 to 31 in FIG. 1). The optical stimuli can, for example, be generated with a time offset by the segments 76 to 79 so that subpopulations with different phases can be formed. A phase-offset generation of the stimuli has the same meaning as the time-offset generation of the stimuli and the result likewise produces a time-offset reset of the phases of the different subpopulations.

Figure 15:
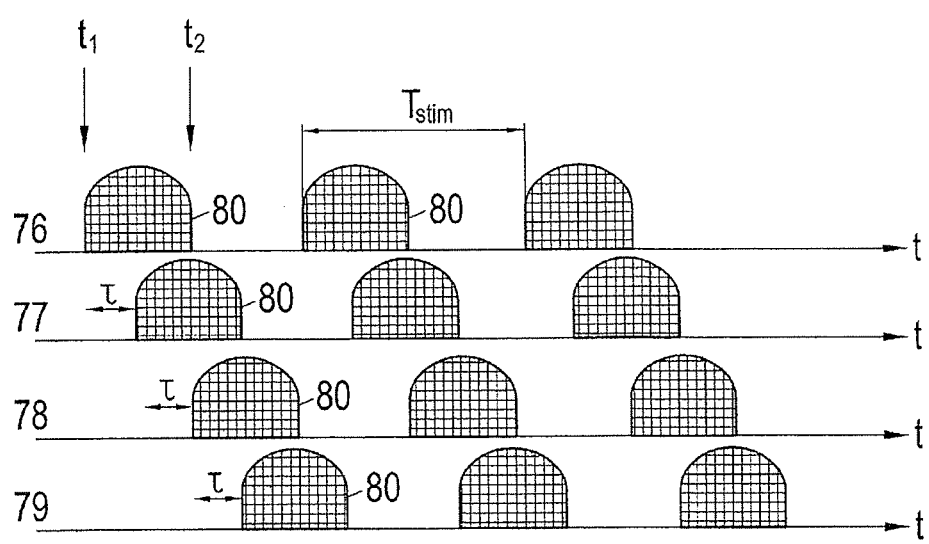
FIG. 15 a schematic representation of visual CR neuromodulation.

A stimulation process which is suitable for the above-described purposes and which can be carried out, for example, with the transmission glasses 75 is shown schematically in FIG. 15. The optical stimuli 80 applied by means of the segments 76 to 79 are entered beneath one another against the time t in FIG. 15 (the segments 76 to 79 correspond to the four channels from FIG. 6). In the embodiment shown in FIG. 15, it is assumed that only the segments 76 to 79 of the transmission glasses 75 generate optical stimuli 80, i.e. only the transmission of these segments is modulated by the control and analysis unit 60. This is naturally only to be understood by way of example. In alternative embodiments, other segments than the segments 76 to 79 can be used for generating the optical stimuli It is possible, as in FIG. 15, only to use a selection of the segments or also all segments of the transmission glasses 75 for the stimulation.

In the process shown in FIG. 15, each of the segments 76 to 79 periodically applies the optical stimulus 80. The stimulus 80 is applied three times per segment 76 to 79 in the present example. Alternatively, the stimulus 145 could also be repeated once to twenty times per sequence, for example. The frequency $f_{stim}=1/T_{stim}$, at which the stimuli 80 are repeated per segment 76 to 79, can lie in the range from 1 to 30 Hz and in particular in the range from 1 to 20 Hz, but can also adopt smaller or larger values. Such sequences of optical stimuli are suitable to reset the neural phase of a stimulated pathological subpopulation of neurons. The frequency $f_{stim}$ can lie, for example, in the range of the mean frequency of the pathologically rhythmic activity of the target network, as has already been explained above.

The structure of a single optical stimulus 80 will be explained in the following with reference to the first stimulus 80 generated by the segment 76. Here, the segment 76 is controlled by the control and analysis unit 60 at the time $t_1$ such that the transmission of the segment 76 is reduced. The control and analysis unit 60 switches the transmission of the segment 76 to the maximum value at the time $t_2$. In other words, this means that the segment 76 becomes less transparent when stimulated. Accordingly, the patient perceives a reduced brightness of the environmental light in the region of the segment 76 during the stimulation.

The individual pulses 80 preferably do not have a rectangular shape, but rather less sharp flanks. Depending e.g. on the basic disease of the patient as well as on individual psychophysical properties, e.g. glare sensitivity, differently configured stimuli, e.g. sinusoidal optical stimuli, can also be used, however.

It is alternatively also possible to increase the transmission of the segment 76 at the time $t_1$ and to switch it to a minimum at the time $t_2$ so that the segment 76 becomes more transparent during the stimulation.

It is generally conceivable to select 100% as the maximum transmission, i.e. in this case the environmental light is not attenuated at all through the respective segment. Such a high transmission can, however, frequently not be reached due to technical limits so that smaller transmission value can be selected for the maximum transmission in the range from 60% to 100%. The minimum transmission can adopt a value in the range from 0% to 30%. However, stimulation successes can also be achieved with transmission values which are outside the stated ranges.

The duration of an optical stimulus 80, i.e. the length of time between the times $t_1$ and $t_2$, can amount to $T_{stim}/2$, for example. In this case, the length of time during which stimulation takes place and the following stimulation phase are of equal length (if stimulation is only over two segments of glasses). It is, however, also possible to select different stimulation durations, for example, in the range from $T_{stim}/2-T_{stim}/10$ to $T_{stim}/2+T_{stim}/10$. Other stimulation durations are also possible and can be determined experimentally, for example.

In accordance with the embodiment shown in FIG. 15, the administration of the optical stimuli 80 takes place over the individual segments 76 to 79 of the transmission glasses 11 with a time delay between the individual segments 76 to 79. The start of stimuli 80 following one another in time and applied by different 76-79 segments can, for example, be displaced by a time τ.

In the case of N stimulation elements or segments which are used for stimulation, the time delay τ between a respective two stimuli 80 following one another can be, for example, in the range of an Nth of the period $T_{stim}=1/f_{stim}$. In the embodiment shown in FIG. 15 (N=4), the time delay τ accordingly amounts to $T_{stim}/4$. It is possible to deviate by a certain amount from the requirement that the time delay τ between a respective two stimuli 80 following one another is $T_{stim}/N$. For example, it is possible to deviate from the value $T_{stim}/N$ for the time delay τ by up to ±5%, ±10% or ±20%. On such a deviation, stimulation successes were still achieved; i.e. a desynchronizing effect was still able to be observed.

The calibration procedure already described above can be carried out for determining the ideal stimulation parameters for an optical CR neuromodulation.

In the first step of the calibration procedure, first optical stimuli which lie in a first visual field range are generated by means of the transmission glasses 75 or by means of another optical stimulation unit. The first visual field region should be covered by the first stimuli in accordance with the physiological mapping characteristics familiar to the skilled person such that the associated target sites in the brain which are stimulated by the first optical stimuli have the same spatial distances from one another, that is are equidistant, in a first approximation.

The first stimuli are subsequently tested by the control and analysis unit 60 as to whether they can reset the phase of the pathological, synchronized and oscillatory brain activity. In this respect, in the second step, those first stimuli are selected from the preselection of first stimuli which can reset the phase of the pathological, synchronized and oscillatory brain activity.

If all the first stimuli from the start selection can reset the phase of the pathological, synchronized and oscillatory brain activity, second stimuli ("marginal stimuli") are added to these first stimuli. The second stimuli are disposed outside the first visual field region, but within a second visual field region which comprises the first visual field region. Those stimuli are also selected from among the second stimuli which can reset the phase of the pathological, synchronized and oscillatory brain activity.

Once the effective, i.e. phase resetting, stimuli have been selected in the second step, the control and analysis unit 60 determines in the third step those third stimuli which stimulate the associated brain area as equidistantly as possible when the eyes look straight ahead. In the event that no second stimuli were selected in the second step, a few further stimuli will be selected distributed over the total effective visual field range beside the outwardly disposed first stimuli in accordance with a physiological scaling familiar to the skilled person (e.g. complexly logarithmic mapping of the retina on the cortex), the further stimuli lying between the two first stimuli disposed outwardly in the effective visual field region. These stimuli form the third stimuli. The target sites of the third stimuli are preferably approximately equidistant in the brain or spinal cord of the patient.

If second stimuli were selected, the second stimuli disposed outwardly in the effective (second) visual field region are selected as the "marginal stimuli" of the third stimuli. Even further third stimuli are distributed between these outer second stimuli.

A CR stimulation is carried out pairwise in each case using the third stimuli, as shown in FIG. 15 (in this case with only two segments of the transmission glasses 75). If this test results in an amplitude increase of the pathological oscillation, the distance of the two third stimuli is varied for so long (by use of different segments of the transmission glasses 75) until the CR stimulation with the stimulus pair no longer shows any amplitude increase in the pathological oscillation. This test is carried out using all adjacent third stimuli.

In the fourth step, the control and analysis unit 60 checks, if all third stimuli determined in the third step are used, whether the associated CR neuromodulation suppresses the pathologically synchronous and oscillatory neural activity of the stimulated neurons and whether it in particular has a desynchronizing effect. A CR stimulation as is shown in FIG. 15 is carried out for this purpose. Such a CR stimulation using all selected third stimuli should produce a reduction in the amplitude of the pathological signal, which corresponds to a CR induced desynchronization of the underlying pathologically synchronized neural population.

Stimulation Units for Generating Tactile, Vibratory, Thermal and/or Electrical Transcutaneous Stimuli:

In the following, embodiments of the non-invasive stimulation unit 11 for generating tactile, vibratory, thermal and/or electrical transcutaneous stimuli 22 are described. Such stimulation units can also be seen from German patent application No. 10 2010 000 390.5 having the title "Apparatus and method for treating a patient with vibratory, tactile and/or thermal stimuli" which was filed with the German Patent and Trademark Office on Feb. 11, 2010. The total disclosure content of German patent application No. 10 2010 000 390.5 is herewith included in the disclosure of the present application.

Figure 16:
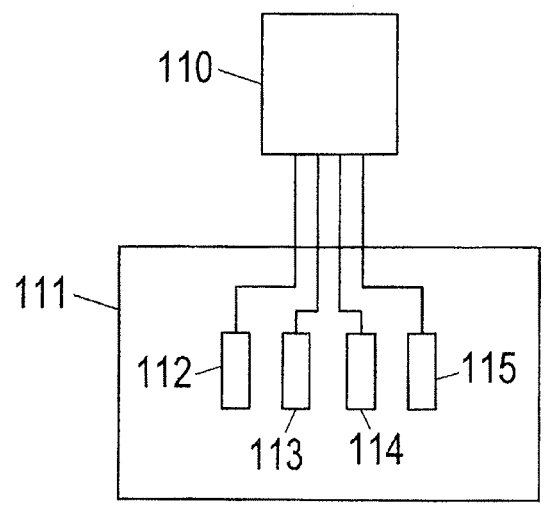
FIG. 16 a schematic representation of an apparatus for tactile, vibratory, thermal and/or electrical transcutaneous desynchronizing neurostimulation.

FIG. 16 schematically shows a control and analysis unit 110 and a stimulation unit 111 controlled by the control and analysis unit 110 (the measuring unit is not shown in FIG. 16). The stimulation unit 111 includes a plurality of stimulation elements for generating tactile, vibratory, thermal and/or electrical transcutaneous stimuli. In the present embodiment, the stimulation unit 111 has four stimulation elements 112, 113, 114 and 115 which are controlled by the control and analysis unit 110. The embodiment shown in FIG. 16 is only to be understood in an exemplary manner. Alternatively to this embodiment, the stimulation unit 111 can include any desired number of stimulation elements.

The stimulation units 112 to 115 are designed such that they can be placed on the skin of the patient. Depending on the disease and/or on the effected parts of the body, the stimulation units 112 to 115 are secured on the skin of the patient in a suitable arrangement, for example to the arm, to the leg, to the hand and/or to the foot of the patient. Tactile, vibratory, thermal and electrical transcutaneous stimuli can be administered either individually or in combination on the skin depending on the symptoms.

The plurality of stimulation elements 112 to 115 make it possible to stimulate different receptive regions of the skin via the individual stimulation elements 112 to 115 with time and space coordination. The stimulation units 112 to 115 can be arranged on the skin of the patient such that the stimuli applied to the skin tissue are forwarded via nerve conductors to different target regions which e.g. lie in the brain and/or in the spinal cord. Consequently, different target zones in the brain and/or spinal cord can be stimulated with possibly different and/or time-offset stimuli during the same stimulation period.

Figure 17A:
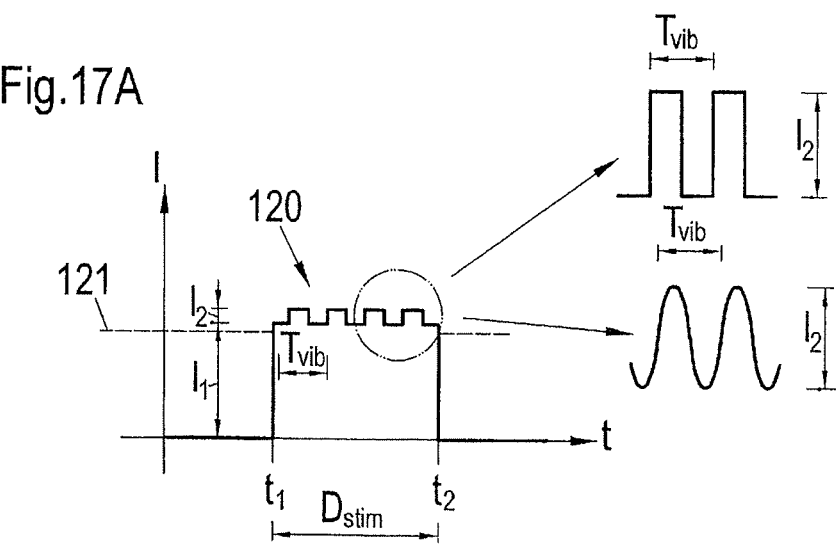
FIGS. 17A and 17B schematic representations of vibratory stimuli.
Figure 17B:
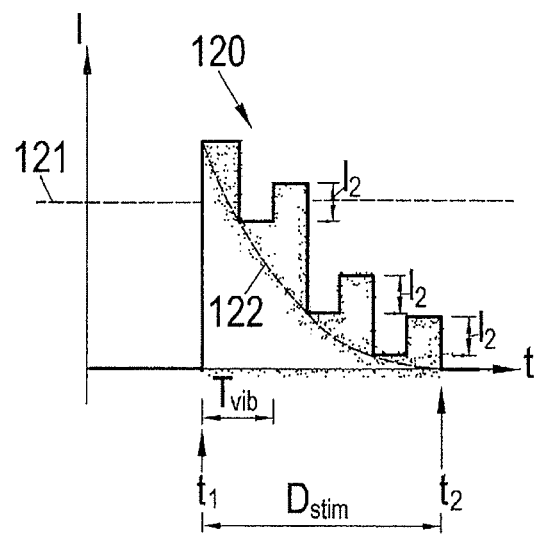

Different embodiments of individual vibratory stimuli 120 are shown in FIGS. 17A and 17B. The deflection 1 of a stimulation element is entered against the time t there. The stimulation element is deflected from its position of rest at the time $t_1$ in FIG. 17A and is pressed into the skin of the patient. The position of the skin surface is shown by a dashed line 121. Once the stimulation element has come into contact with the skin, a periodic vibratory stimulus is applied at a frequency $f_{vib}=1$ $T_{vib}$ in the range from 5 to 300 Hz ($T_{vib}$=period duration of the vibration stimulus). At a frequency $f_{vib}$ of 300 Hz, the stimulation element can exert a force of approximately 2 N. The duration $D_{stim}$ of the vibration stimulus 120 can lie in the range from 10 to 500 ms.

At the time $t_2$, the stimulation element is again moved to its position of rest where it has no contact with the skin. As shown in FIG. 17A, the vibratory stimulus 120 can be a rectangular or sinusoidal stimulus, but it can also have different forms. The deflection $1_1$ shown in FIG. 17A for pressing the stimulation element into the skin can lie in the range from 0.5 to 3 mm. The deflection $1_2$ of the stimulation element during the vibration can amount to between 0.1 and 0.5 mm.

Provision can alternatively be made that the stimulation element is always in contact with the skin of the patient and a purely vibratory stimulus is applied during the stimulation period $D_{stim}$.

A further variant of the vibratory stimulus 120 is shown in FIG. 17B. Unlike the embodiment shown in FIG. 17A, the stimulation element is already retracted again during the stimulation period $D_{stim}$ so that the vibrations press less into the skin as the time period grows and the stimulation element is finally completely released from the skin. The retraction of the stimulation element can take place, for example, along a linear or non-linear, e.g. exponential, curve 122 on which the vibrations $f_{vib}$ of the stimulation element are superposed. In the example shown in FIG. 17B the falling flank of each pulse extends down to the curve 122. The adjoining pulse has a fixedly preset height $1_2$, i.e. the rising flank of each pulse has the height $1_2$.

Figure 18:
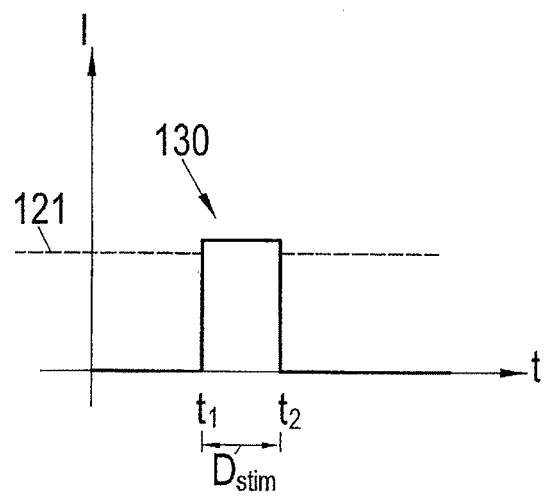
FIG. 18 a schematic representation of a tactile stimulus.

An embodiment of a tactile stimulus 130 is shown in FIG. 18. The stimulation element is pressed into the skin of the patent at the time $t_1$, remains there for the stimulation duration $D_{stim}$ and is retracted again at the time $t_2$. The stimulation duration $D_{stim}$ lies in the range from 10 to 500 ms with a tactile stimulation 130.

Stimulation elements for generating tactile and/or vibratory stimuli can be designed, for example, as a bar or as a stamp with whose one end the skin of the patient is stimulated. The end of the stimulation element which comes into contact with the skin surface and ultimately generates the stimuli can, for example, substantially have the shape of a hemisphere or can have a nub-like surface or any other suitable shape. The stimulation element is driven by an electromechanical converter (or actor or actuator) which converts electric energy into a movement of the stimulation element. DC motors, voice coils, piezoelectric converters or converters comprising electroactive polymers (EAPs) which change their shape on application of an electric voltage are, for example, suitable as electromechanical converters.

Figure 19A:
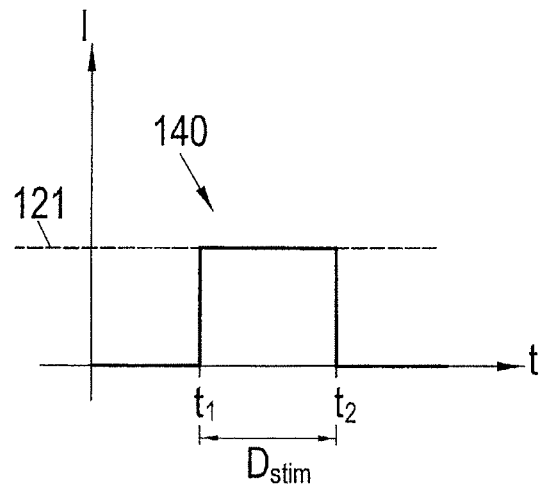
FIGS. 19A and 19B schematic representations of thermal stimuli.
Figure 19B:
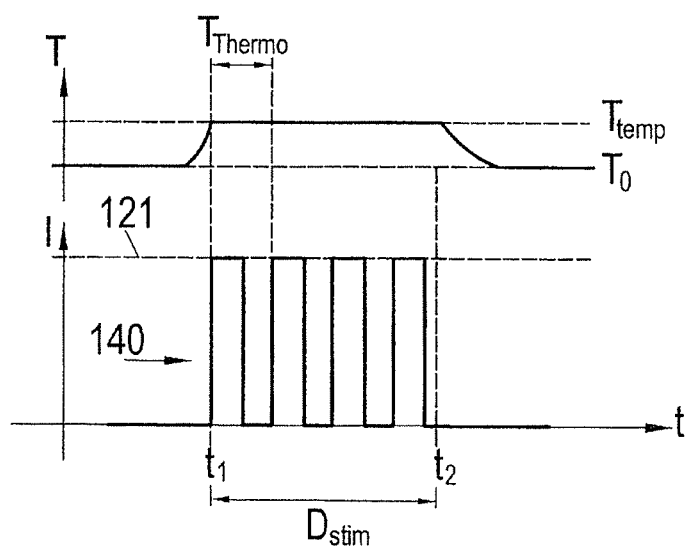

Various embodiments of individual thermal stimuli 140 are shown in FIGS. 19A and 19B. In both embodiments, a stimulation element is heated or cooled to a temperature $T_{temp}$. As is shown in FIG. 19B, the temperature $T_{temp}$ can only be generated just before the application of the thermal stimulus 140. In this case, the stimulation element has a temperature $T_0$ during the stimulation pauses which corresponds e.g. to the room temperature. Alternatively, the stimulation element can be held at a constant temperature $T_{temp}$.

In the embodiment in accordance with FIG. 19A, the heated or cooled stimulation element is applied to the skin of the patient at the time $t_1$ and remains there for the total stimulation duration $D_{stim}$. In contrast to this, in the embodiment in accordance with FIG. 19B, the stimulation element is applied periodically to the skin with a frequency $f_{thermo}$ during the stimulation duration $D_{stim}$ and is removed again. The frequency $f_{thermo}=1/T_{thermo}$ can lie in the range of 1 to 10 Hz ($T_{thermo}$=period duration of the thermal stimulation).

Stimulation elements which apply thermal stimuli by contact of the skin surface can be configured, for example in bar shape and can include heating and/or cooling elements (e.g. in the form of heating loops) which heat or cool the stimulation elements. Electromechanical converters can provide the movement of the stimulation elements.

In a further variant, the thermal stimuli 140 is generated non-contactlessly. The stimulation temperature $T_{temp}$ is here generated by electromagnetic radiation, for example by infrared light. Furthermore, the electromagnetic radiation is periodically varied with the frequency $f_{thermo}=1/T_{thermo}$ (e.g. by switching an infrared radiator on and off).

With thermal stimuli 140, the stimulation duration $D_{stim}$ lies in the range from 10 to 500 ms. The temperature $T_{temp}$ can be from 22 to 42° C. The temperature To is as a rule the body temperature of the patient. The frequency $f_{thermo}$ can lie between 1 and 10 Hz, but can also lie outside this range.

FIG. 20 shows an electrical transcutaneous stimulus 150 in which a current pulse train or voltage pulse train is applied to the skin of the patient for the duration $D_{stim}$. The electrical transcutaneous stimulus 150 can be generated by a metal electrode fastened to the skin of the patient.

The electrical transcutaneous stimuli can e.g. be charge-balanced individual rectangular pulses or pulse trains having a plurality (e.g. 1 to 100) charge-balanced individual rectangular pulses. The pulse train 150 shown by way of example in FIG. 20 comprises three individual pulses 180 which are repeated at a frequency $f_{Puls}=1/T_{Puls}$ in the range from 1 to 150 Hz, in particular in the range from 60 to 150 Hz. The individual pulses 180 can be current-controlled or voltage-controlled pulses which are composed of an initial pulse portion 181 and a pulse portion 182 following it and flowing in the opposite direction, with the polarity of the two pulse portions 181 and 182 also being able to be swapped over with respect to the polarity shown in FIG. 20. The duration 183 of the pulse portion 181 lies in the range between 1 μs and 450 μs. The amplitude 184 of the pulse portion 181 lies in the case of current-controlled pulses in the range between 0 mA and 25 mA and in the case of voltage-controlled pulses in the range from 0 to 20 V. The amplitude of the pulse portion 182 is smaller than the amplitude 184 of the pulse portion 181. In turn the duration of the pulse portion 182 is longer than that of the pulse portion 181. The pulse portions 181 and 182 are ideally dimensioned such that the charge which is transferred by them is of equal magnitude in both pulse portions 181 and 182, i.e. the surfaces drawn hatched in FIG. 20 are of equal size. Accordingly, just as much charge is introduced into the tissue by an individual pulse 180 as is removed from the tissue.

The rectangular shape of the individual pulses 180 shown in FIG. 20 represents an ideal form. There is a deviation from the ideal rectangular shape in dependence on the quality of the electronics generating the individual pulses 180.

Instead of pulse-shaped stimuli, differently configured stimuli can also be used, e.g. time-continuous stimulus patterns such as charge-balanced sinusoidal stimuli, for instance. The sinusoidal stimuli can either last exactly one sine period or a whole-number number of sine periods to ensure that the stimuli are charge-balanced. The frequency of the sinusoidal oscillations can lie in the range from 1 to 150 Hz and in particular in the range from 60 to 150 Hz.

The stimuli applied by the stimulation units 112 to 115 are received by receptors disposed in or beneath the skin and are forwarded to the nervous system. These receptors include, for example, Merkel cells, Ruffini corpuscles, Meissner's corpuscles and hair follicle receptors which in particular act as receptors for the tactile stimuli. The vibratory stimuli primarily focus on the proprioception and are received by receptors disposed in the skin, in the muscles, in the subcutaneous tissue and/or in the tendons of the patient. Pacini's corpuscles, which communicate vibration perceptions and accelerations, can be named as examples for the vibration stimuli. The thermal stimuli are received by the thermoreceptors of the skin. They are warm receptors (also called heat receptors, warm sensors or heat sensors) and cold sensors (also called cold receptors). The cold sensors are more superficial in the skin of people; the heat receptors somewhat lower. The electrical transcutaneous stimuli are largely non-specific and are received by different receptors disposed in or beneath the skin.

The stimuli 120 to 150 generated by the stimulation elements 112 to 115 are designed such that they effect a reset of the phase of neural activity of the stimulated neurons when they are received by the corresponding receptors and are conducted via the nerve conductors to a neural population in the brain or spinal cord with a pathological synchronous and oscillatory activity. The pathological neural population can be stimulated at different sites due to the plurality of stimulation elements 112 to 115. This makes it possible to reset the phase of neural activity of the pathological neural population at the different stimulation points at different times. As a result, the pathological neural population whose neurons were previously active synchronously and at the same frequency and phase are split into a plurality of subpopulations. The desynchronization of the previously pathologically synchronous neural population can be effected by such a CR neural modulation.

A CR stimulation carried out with the aid of stimulation elements 112 to 115 is shown schematically in FIG. 21. The respective receptors are stimulated at different points of the skin of the patient using tactile and/or vibratory and/or thermal and/or electrical transcutaneous stimuli 120 to 150 via the stimulation elements 112 to 115.

In the embodiment shown in FIG. 21, each of the stimulation elements 112 to 115 applies a stimulus 120 to 150 periodically at the frequency $f_{stim}=1/T_{stim}$. The frequency $f_{stim}$ can lie in the range from 1 to 60 Hz and in particular in the range from 30 to 60 Hz or in the range from 1 to 30 Hz or in the range 1 to 20 Hz or in the region from 5 to 20 Hz, but can also adopt smaller or larger values. The frequency $f_{stim}$ can in particular lie close to the mean frequency of the pathologically rhythmic activity of the target network.

The administering of the stimuli 120 to 150 via different simulation elements 112 to 115 takes place with a time delay τ between the individual stimulation elements 112 to 115 by $T_{stim}/4$.

In the case of N stimulation elements, the time delay τ between two respective successive stimuli 120 to 150 can lie, for example in the range of an Nth of the period $1/f_{stim}$, i.e. $1/N \times f_{stim})=T_{stim}/N$, i.e. the time $T_{stim}/N$ in particular elapses between the starting times of two stimuli 120 to 150 following one another. It is possible to deviate to a certain degree from the requirement that the time delay τ between two stimuli following one another amounts to $T_{stim}/T$. For example, it is possible to deviate from the value $T_{stim}/N$ for the time delay τ by up to ±5%, ±10% or ±20%. Stimulation successes are achieved on such a deviation, i.e. a desynchronizing effect could be observed.

The stimuli 120 to 150 applied by the stimulation elements 112 to 115 are forwarded to different subpopulations of the neural population (cf. e.g. neural population 27 with subpopulations 28 to 31 in FIG. 1) and reset the phases of these subpopulations at respective different times, whereby a desynchronization of the total neural population is achieved.

The direct stimulation of specific regions of the brain or of the spinal cord is made possible by the somatotopic association of body regions with these regions. The stimulation units 112 to 115 can be applied, for example, to the foot, lower leg and thigh or to the hand, the lower arm and upper arm of the patient. Different neurons are stimulated by the stimuli applied to the respective points due to the somatotopic structure of the neural pathways. The somatotopic association of skin points with regions of the brain is described for example in A. Benninghoff et al.: "Lehrbuch der Anatomie des Menschen. Nervensystem, Haut und Sinnesorgane", [Textbook of Human Anatomy. Presented With Emphasis on Functional Relationships. 3rd Vol., Nervous System, Skin and Sensory Organs", Urban und Schwarzenberg, Munich 1964.

Figure 22:
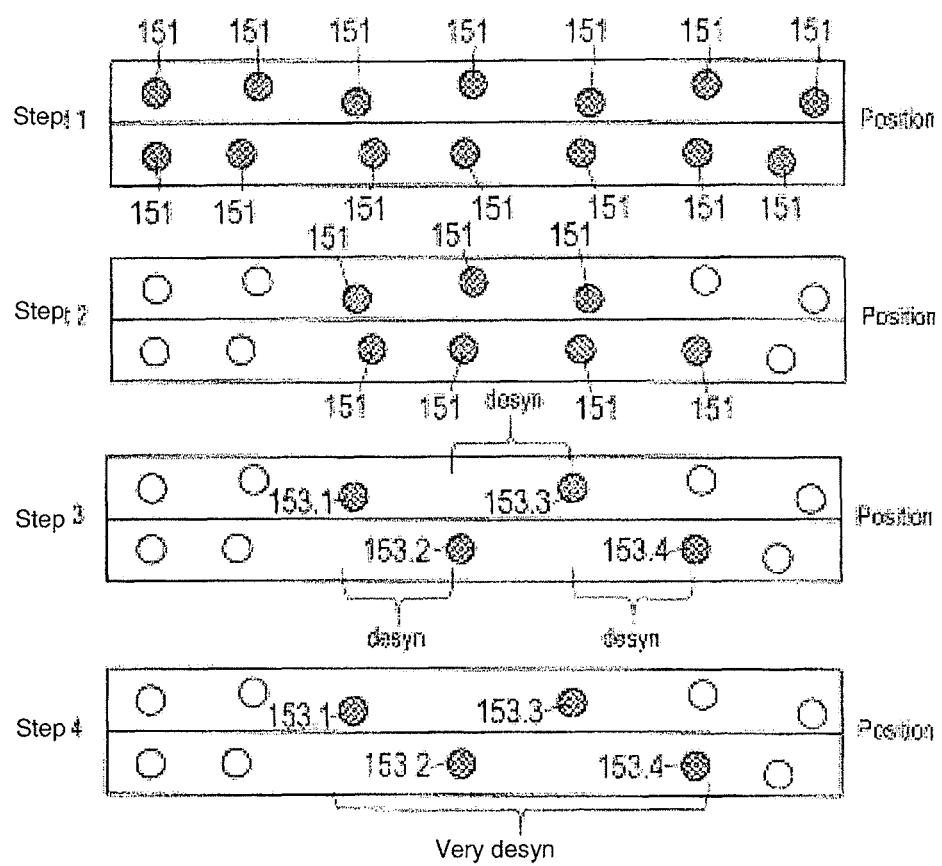
FIG. 22 a flowchart for illustrating the calibration of the apparatus shown in FIG. 16.

The calibration procedure already explained above can be carried out for determining the ideal stimulus parameters for the tactile, vibratory, thermal and/or electrical transcutaneous CR neuromodulation. A flowchart to illustrate the process routine of the calibration is shown in FIG. 22. The front side (top) and lower side (bottom) of the arm of a patient is shown schematically for each of the four calibration steps there. The hand (not shown) is at the right; the shoulder (not shown) is at the left. The positions of the stimulation elements are shown respectively for the front side and rear side of the arm in FIG. 22. The stimulation elements can, for example, be fastened to the arm of the patient using hook and loop fasteners, whereby the position of the stimulation elements can easily be changed.

In the first step, a first skin area is selected which includes the diseased body part (that is is a littler larger so that the actually required extent can be determined by the selection of the ideal individual stimuli) or representations (e.g. Head's zones) of the diseased body part or organ. Tactile, vibratory, thermal and/or electrical transcutaneous first stimuli 151 are applied to the positions shown in FIG. 22 within the selected first skin area. In this respect, the two-dimension starting area of the skin is covered with the first stimuli 151 in accordance with the physiological somatotopic mapping characteristics such that the associated target zones in the brain which are stimulated by the first stimuli 151 have the same spatial distances from one another, that is are equidistant, in a first approximation.

The first stimuli 151 are now tested by the control and analysis unit 110 as to whether they can reset the phase of the pathological, synchronized oscillatory brain activity. In this respect, those first stimuli 151 are selected from the preselection of first stimuli 151 which can reset the phase of the pathological, synchronized and oscillatory brain activity. FIG. 22 shows by way of example the first stimuli 151 selected in this respect in step 2. The non-effective, i.e. non phase-resetting and accordingly discarded, first stimuli 151 are shown as non-filled in circles in step 2.

If all the first stimuli 151 from the start selection, i.e. all the first stimuli 151 shown in step 1 of FIG. 22, can reset the phase of the pathological, synchronized and oscillatory brain activity, second stimuli ("marginal stimuli") (not shown in FIG. 22) are added to these first stimuli 151. The second stimuli are outside the first skin area, but within a second skin area comprising the first skin area. Those stimuli are also selected from among the second stimuli which can reset the phase of the pathological, synchronized and oscillatory brain activity.

Once the effective, i.e. phase-resetting, stimuli have been selected in the second step, the control and analysis unit 110 determine in the third step those third stimuli 153 which stimulate the associated brain area as equidistantly as possible. The procedure is as follows for this purpose. In the event that no second stimuli were selected in the second step, a few further stimuli are selected distributed over the total effective skin area beside the outwardly disposed first stimuli 151 in accordance with somatotopic association familiar to the skilled person, said further stimuli lying between the two outwardly disposed effective first stimuli 151. These stimuli form the third stimuli 153. Four third stimuli 153.1, 153.2, 153.3 and 153.4 are shown by way of example in FIG. 22. The target sites of the third stimuli 153.1 to 153.4 are preferably approximately equidistant in the brain or spinal cord of the patient.

If second stimuli were selected in the second step, the second stimuli outwardly disposed in the effective (second) skin area are selected as "marginal stimuli" of the third stimuli 153 (in accordance with the stimuli 153.1 and 153.4 of FIG. 22). Still further third stimuli (corresponding to the stimuli 153.2 and 153.3 from FIG. 22) are distributed between these outer second stimuli.

A CR stimulation such as is shown in FIG. 21 is carried out respectively pairwise using the third stimuli 153.1 to 153.4 (in this case with only two channels). The stimulus pair 153.1/153.2 is first tested. If this test produces an amplitude increase in the pathological oscillation (that is an amplification of the synchronization of the pathologically synchronized neural population generating the signal), the stimulation element generating the stimulus 153.2 is displaced further from the stimulation element generating the stimulus 153.1 for so long until the CR stimulation with the stimulus pair 153.1/153.2 no longer shows any amplitude increase in the pathological oscillation. The stimulus pair 153.2/153.3 is subsequently tested in the same way. If necessary, the stimulation element generating the stimulus 153.3 is displaced here until the amplitude of the pathological oscillation no longer grows in the CR stimulation. The stimulus pair 153.3/153.4 is then tested. It can occur in this respect that the outermost stimulus 153.4 migrates out of the second skin area. In this case, one of the third stimuli, e.g. the stimulus 153.3, can optionally be discarded. The test would then be carried out using the stimulus pair 153.2/153.4.

In the fourth step, the control and analysis unit 110 checks whether, on the use of all third stimuli 153.1 to 153.4 determined in the third step, the associated CR stimulation suppresses the pathologically synchronous and oscillatory neural activity of the stimulated neurons and in particular has a desynchronizing effect. A CR stimulation as is shown in FIG. 21 is carried out for this purpose. Such a CR stimulation with all selected third stimuli 153.1 to 153.4 should produce a fall in the amplitude of the pathological signal, which corresponds to a CR-induced desynchronization of the underlying pathologically synchronized neural population.

The invention claimed is:

1. An apparatus for stimulating neurons with a pathologically synchronous and oscillatory neural activity, the apparatus comprising:
a non-invasive stimulation unit for applying stimuli to a patient, wherein the stimuli stimulate neurons of the patient;
a measuring unit for recording measured signals which reproduce a neural activity of the stimulated neurons;
a control and analysis unit for controlling the stimulation unit and for analyzing the measured signals, wherein the control and analysis unit is configured to:
control the stimulation unit to apply first stimuli, wherein the first stimuli each have a stimulus parameter that lies within a first stimulus parameter range for all first stimuli,
select the first stimuli that effects a phase reset of the pathologically synchronous and oscillatory neural activity of the stimulated neurons with reference to the measured signals recorded in response to the application of the first stimuli,
select a second stimuli, wherein the selected first stimuli disposed at the boundary or outside the first stimulus parameter range as well as further stimuli disposed between these first stimuli belong to the second stimuli,
control the stimulation unit to apply two of the second stimuli with a time offset, and
check with reference to the measured signals recorded in response to the second stimuli applied with a time offset whether the second stimuli applied with a time offset effect an increase in the pathologically synchronous and oscillatory activity of the neurons.

2. The apparatus according to claim 1, wherein the control and analysis unit is further configured to vary the stimulus parameter of one of the two second stimuli if the two second stimuli applied with a time offset effect an increase in the pathologically synchronous and oscillatory activity of the neurons.

3. The apparatus according to claim 2, wherein the variation of the stimulus parameter of the one of the two third stimuli enlarges the tonotopic distance between the two third stimuli.

4. An apparatus for stimulating neurons with a pathologically synchronous and oscillatory neural activity, the apparatus comprising:
- a non-invasive stimulation unit for applying stimuli to a patient, wherein the stimuli stimulate neurons of the patient;
- a measuring unit for recording measured signals which reproduce a neural activity of the stimulated neurons;
- a control and analysis unit for controlling the stimulation unit and for analyzing the measured signals, wherein the control and analysis unit is configured to:
  - control the stimulation unit to apply first stimuli, wherein the first stimuli each have a stimulus parameter that lies within a first stimulus parameter range for all first stimuli,
  - select the first stimuli that effects a phase reset of the pathologically synchronous and oscillatory neural activity of the stimulated neurons with reference to the measured signals recorded in response to the application of the first stimuli,
  - control the stimulation unit to apply second stimuli if all the applied first stimuli effect a phase reset of the pathologically synchronous and oscillatory neural activity of the stimulated neurons, wherein the second stimuli each have a stimulus parameter which lies outside the first stimulus parameter range and within a second stimulus parameter range for all second stimuli,
  - selects the second stimuli that effect a phase reset of the pathologically synchronous and oscillatory neural activity of the stimulated neurons with reference to the measured signals recorded in response to the application of the second stimuli,
  - form a selection of third stimuli, wherein the selected second stimuli disposed outwardly in the second stimulus parameter range as well as further stimuli disposed between these second stimuli belong to the third stimuli,
  - control the stimulation unit to apply two of the third stimuli with a time offset, and
  - determine with reference to the measured signals recorded in response to the third stimuli applied with the time offset whether the third stimuli applied with the time offset effect an increase in the pathologically synchronous and oscillatory activity of the neurons.

5. The apparatus according to claim 4, wherein the control and analysis unit is further configured to vary the stimulus parameter of one of the two third stimuli if the two third stimuli applied with a time offset effect an increase in the pathologically synchronous and oscillatory activity of the neurons.

6. The apparatus according to claim 5, wherein the variation of the stimulus parameter of the one of the two third stimuli enlarges a tonotopic distance between the two third stimuli.

7. The apparatus according to claim 4, wherein the control and analysis unit is configured to select the first stimuli such that respective target sites in the brain of the patient are approximately equidistant.

8. The apparatus according to claim 4, wherein the stimulation unit is configured to generate acoustic stimuli.

9. The apparatus according to claim 8, wherein,
the stimulus parameter is a frequency and the first and second stimulus parameter ranges are each a frequency interval.

\* \* \* \* \*